(12) United States Patent
Shaolian et al.

(10) Patent No.: US 11,298,230 B2
(45) Date of Patent: Apr. 12, 2022

(54) PERCUTANEOUS ANNULOPLASTY SYSTEM WITH ANTERIOR-POSTERIOR ADJUSTMENT

(71) Applicant: VALCARE, INC., Newport Beach, CA (US)

(72) Inventors: Samuel M. Shaolian, Newport Beach, CA (US); Jeffrey P. Dumontelle, Irvine, CA (US); Nadav Yellin, Irvine, CA (US); Victor S. Packham, Costa Mesa, CA (US); Hung H. Cao, Corona, CA (US)

(73) Assignee: VALCARE, INC., Newport Beach, CA (US)

( * ) Notice: Subject to any disclaimer, the term of this patent is extended or adjusted under 35 U.S.C. 154(b) by 28 days.

(21) Appl. No.: 15/838,241

(22) Filed: Dec. 11, 2017

(65) Prior Publication Data

US 2018/0161160 A1    Jun. 14, 2018

Related U.S. Application Data

(62) Division of application No. 13/779,478, filed on Feb. 27, 2013, now Pat. No. 9,839,519.

(Continued)

(51) Int. Cl.
*A61F 2/24*    (2006.01)

(52) U.S. Cl.
CPC .......... *A61F 2/2448* (2013.01); *A61F 2/2466* (2013.01); *A61F 2220/0016* (2013.01); *A61F 2250/001* (2013.01); *F04C 2270/0421* (2013.01)

(58) Field of Classification Search
CPC .... A61F 2/2409; A61F 2/2445; A61F 2/2466; A61F 2/243; A61F 2/2442; A61F 2/2448;
(Continued)

(56) References Cited

U.S. PATENT DOCUMENTS

| 4,602,911 A | 7/1986 | Ahmadi et al. |
|---|---|---|
| 5,236,440 A | 8/1993 | Hlavacek |

(Continued)

FOREIGN PATENT DOCUMENTS

| DE | 102014102653 A1 | 9/2015 |
|---|---|---|
| EP | 1752115 A1 | 2/2007 |

(Continued)

OTHER PUBLICATIONS

Communication pursuant to Article 94(3) EPC for EP 14801009.3 dated Sep. 27, 2018.

(Continued)

*Primary Examiner* — Todd J Scherbel
*Assistant Examiner* — Mikail A Mannan
(74) *Attorney, Agent, or Firm* — Stoel Rives LLP

(57) ABSTRACT

Apparatus, systems, and methods are provided for repairing heart valves through percutaneous transcatheter delivery and fixation of annuloplasty rings to heart valves. An annuloplasty ring includes an outer hollow body member including a plurality of regions. Adjacent regions cooperate with one another to change the body member from an elongate insertion geometry to an annular operable geometry. Adjacent regions are coupled by a biasing element or a stepped connector to allow expansion to an expanded state and contraction to a contracted state in the annular operable geometry. The annuloplasty ring also includes an internal anchor member located at least partially within the body member and having a plurality of anchors configured to attach the annuloplasty ring to tissue of a heart valve annulus. An angled ring closure lock allows coupling of the ends of an annuloplasty ring at an apex of a D-shape annular operable geometry.

16 Claims, 30 Drawing Sheets

Related U.S. Application Data

(60) Provisional application No. 61/734,904, filed on Dec. 7, 2012, provisional application No. 61/604,856, filed on Feb. 29, 2012.

(58) Field of Classification Search
CPC .... A61F 2/2451; A61F 2/2454; A61F 2/2457; A61F 2/2427; A61B 2017/00783; A61B 2017/00243
See application file for complete search history.

(56) References Cited

U.S. PATENT DOCUMENTS

| | | |
|---|---|---|
| 5,306,296 A | 4/1994 | Wright et al. |
| 5,695,518 A | 12/1997 | Laerum |
| 5,716,370 A | 2/1998 | Williamson, IV et al. |
| 5,855,614 A | 1/1999 | Stevens et al. |
| 6,113,611 A | 9/2000 | Allen et al. |
| 6,231,602 B1 | 5/2001 | Carpentier et al. |
| 6,619,291 B2 | 9/2003 | Hlavka et al. |
| 6,629,534 B1 | 10/2003 | St. Goar et al. |
| 6,669,687 B1 | 12/2003 | Saadat |
| 6,689,048 B2 | 2/2004 | Vanden Hoek et al. |
| 6,726,704 B1 | 4/2004 | Loshakove et al. |
| 6,776,784 B2 | 8/2004 | Ginn |
| 6,790,229 B1 | 9/2004 | Berreklouw |
| 6,797,002 B2 | 9/2004 | Spence et al. |
| 6,805,711 B2 | 10/2004 | Quijano et al. |
| 6,893,459 B1 | 5/2005 | Macoviak |
| 7,101,395 B2 | 9/2006 | Tremulis et al. |
| 7,114,953 B1 | 10/2006 | Wagner |
| 7,175,660 B2 | 2/2007 | Cartledge et al. |
| 7,238,191 B2 | 7/2007 | Bachmann |
| 7,285,087 B2 | 10/2007 | Moaddeb et al. |
| 7,297,150 B2 | 11/2007 | Cartledge et al. |
| 7,569,072 B2 | 8/2009 | Berg et al. |
| 7,594,887 B2 | 9/2009 | Moaddeb et al. |
| 7,635,329 B2 | 12/2009 | Goldfarb et al. |
| 7,655,040 B2 | 2/2010 | Douk et al. |
| 7,717,954 B2 | 5/2010 | Solem et al. |
| 7,722,668 B2 | 5/2010 | Moaddeb et al. |
| 7,758,637 B2 | 7/2010 | Starksen et al. |
| 7,837,729 B2 | 11/2010 | Gordon et al. |
| 7,988,725 B2 | 8/2011 | Gross et al. |
| 8,163,014 B2 | 4/2012 | Lane et al. |
| 8,182,529 B2 | 5/2012 | Gordon et al. |
| 8,236,049 B2 | 8/2012 | Rowe et al. |
| 8,287,591 B2 | 10/2012 | Keidar et al. |
| 8,518,107 B2 | 8/2013 | Tsukashima et al. |
| 8,579,968 B1 | 11/2013 | Shannon et al. |
| 9,180,008 B2 | 11/2015 | Yellin et al. |
| 2002/0151961 A1* | 10/2002 | Lashinski ............. A61F 2/2451 623/1.15 |
| 2002/0151970 A1 | 10/2002 | Garrison et al. |
| 2002/0188170 A1 | 12/2002 | Santamore et al. |
| 2002/0198526 A1 | 12/2002 | Shaolian et al. |
| 2003/0050693 A1 | 3/2003 | Quijano et al. |
| 2003/0078465 A1 | 4/2003 | Pai et al. |
| 2003/0078671 A1 | 4/2003 | Lesniak et al. |
| 2003/0191528 A1 | 10/2003 | Quijano et al. |
| 2003/0198605 A1 | 10/2003 | Montgomery |
| 2003/0199974 A1 | 10/2003 | Lee et al. |
| 2004/0044364 A1 | 3/2004 | DeVries et al. |
| 2004/0068276 A1 | 4/2004 | Golden et al. |
| 2004/0122514 A1 | 6/2004 | Fogarty et al. |
| 2004/0138744 A1 | 7/2004 | Lashinski et al. |
| 2004/0148021 A1 | 7/2004 | Cartledge et al. |
| 2004/0193191 A1 | 9/2004 | Starksen et al. |
| 2004/0243230 A1 | 12/2004 | Navia et al. |
| 2004/0249391 A1 | 12/2004 | Cummins |
| 2004/0260393 A1 | 12/2004 | Rahdert et al. |
| 2004/0260394 A1 | 12/2004 | Douk et al. |
| 2005/0020696 A1 | 1/2005 | Montgomery et al. |
| 2005/0033325 A1 | 2/2005 | May et al. |
| 2005/0065550 A1 | 3/2005 | Starksen et al. |
| 2005/0090846 A1 | 4/2005 | Pedersen et al. |
| 2005/0096740 A1 | 5/2005 | Langberg et al. |
| 2005/0113910 A1 | 5/2005 | Paniagua et al. |
| 2005/0137692 A1 | 6/2005 | Haug et al. |
| 2005/0137695 A1 | 6/2005 | Salahieh et al. |
| 2005/0203549 A1 | 9/2005 | Realyvasquez |
| 2005/0222678 A1 | 10/2005 | Lashinski et al. |
| 2005/0240200 A1 | 10/2005 | Bergheim |
| 2005/0267572 A1 | 12/2005 | Schoon et al. |
| 2005/0283190 A1 | 12/2005 | Huitema et al. |
| 2005/0288778 A1 | 12/2005 | Shaoulian et al. |
| 2005/0288781 A1 | 12/2005 | Moaddeb et al. |
| 2006/0009737 A1 | 1/2006 | Whiting et al. |
| 2006/0020327 A1 | 1/2006 | Lashinski et al. |
| 2006/0129025 A1 | 6/2006 | Levine et al. |
| 2006/0155165 A1 | 7/2006 | Vanden Hoek et al. |
| 2006/0161169 A1 | 7/2006 | Nieminen et al. |
| 2006/0184240 A1 | 8/2006 | Jimenez et al. |
| 2006/0184242 A1 | 8/2006 | Lichtenstein |
| 2006/0195134 A1 | 8/2006 | Crittenden |
| 2006/0195183 A1 | 8/2006 | Navia et al. |
| 2006/0241748 A1 | 10/2006 | Lee et al. |
| 2006/0282161 A1 | 12/2006 | Huynh et al. |
| 2007/0016287 A1 | 1/2007 | Cartledge et al. |
| 2007/0027533 A1 | 2/2007 | Douk |
| 2007/0038296 A1 | 2/2007 | Navia |
| 2007/0051377 A1 | 3/2007 | Douk et al. |
| 2007/0067027 A1 | 3/2007 | Moaddeb et al. |
| 2007/0073098 A1 | 3/2007 | Lenker et al. |
| 2007/0080188 A1 | 4/2007 | Spence et al. |
| 2007/0093854 A1 | 4/2007 | Kayan |
| 2007/0118215 A1 | 5/2007 | Moaddeb |
| 2007/0128132 A1 | 6/2007 | Piergallini et al. |
| 2007/0135913 A1 | 6/2007 | Moaddeb et al. |
| 2007/0142907 A1 | 6/2007 | Moaddeb et al. |
| 2007/0213812 A1* | 9/2007 | Webler ............. A61B 17/00234 623/2.11 |
| 2007/0233239 A1 | 10/2007 | Navia et al. |
| 2007/0239272 A1 | 10/2007 | Navia et al. |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0250161 A1 | 10/2007 | Dolan |
| 2007/0293942 A1 | 12/2007 | Mirzaee |
| 2008/0177380 A1 | 7/2008 | Starksen et al. |
| 2008/0177381 A1 | 7/2008 | Navia et al. |
| 2008/0200980 A1 | 8/2008 | Robin et al. |
| 2008/0243220 A1 | 10/2008 | Barker |
| 2008/0262513 A1 | 10/2008 | Stahler et al. |
| 2008/0262609 A1 | 10/2008 | Gross et al. |
| 2008/0306586 A1 | 12/2008 | Cartledge et al. |
| 2009/0088838 A1 | 4/2009 | Shaolian et al. |
| 2009/0118747 A1 | 5/2009 | Bettuchi et al. |
| 2009/0125098 A1 | 5/2009 | Chuter |
| 2009/0149872 A1 | 6/2009 | Gross et al. |
| 2009/0216322 A1 | 8/2009 | Le et al. |
| 2009/0222083 A1 | 9/2009 | Nguyen et al. |
| 2009/0238778 A1 | 9/2009 | Mordas et al. |
| 2009/0299470 A1 | 12/2009 | Rao et al. |
| 2010/0010616 A1 | 1/2010 | Drews et al. |
| 2010/0030014 A1 | 2/2010 | Ferrazzi |
| 2010/0063586 A1 | 3/2010 | Hasenkam et al. |
| 2010/0121433 A1 | 5/2010 | Bolling et al. |
| 2010/0161047 A1 | 6/2010 | Cabiri |
| 2010/0185274 A1 | 7/2010 | Moaddeb et al. |
| 2010/0211166 A1 | 8/2010 | Miller et al. |
| 2010/0249920 A1 | 9/2010 | Bolling et al. |
| 2010/0266989 A1 | 10/2010 | Piergallini et al. |
| 2010/0280604 A1 | 11/2010 | Zipory et al. |
| 2010/0280605 A1 | 11/2010 | Hammer et al. |
| 2010/0286767 A1 | 11/2010 | Zipory et al. |
| 2011/0022168 A1 | 1/2011 | Cartledge |
| 2011/0027753 A1 | 2/2011 | Maurat et al. |
| 2011/0034953 A1 | 2/2011 | Milo |
| 2011/0066231 A1 | 3/2011 | Cartledge et al. |
| 2011/0093062 A1 | 4/2011 | Cartledge et al. |
| 2011/0106245 A1 | 5/2011 | Miller et al. |
| 2011/0106247 A1 | 5/2011 | Miller et al. |

(56) References Cited

U.S. PATENT DOCUMENTS

| | | |
|---|---|---|
| 2011/0137397 A1 | 6/2011 | Chau et al. |
| 2011/0166649 A1 | 7/2011 | Gross et al. |
| 2011/0190879 A1 | 8/2011 | Bobo et al. |
| 2011/0208298 A1 | 8/2011 | Tuval et al. |
| 2011/0224785 A1 | 9/2011 | Hacohen |
| 2011/0257728 A1 | 10/2011 | Kuehn |
| 2011/0282361 A1 | 11/2011 | Miller et al. |
| 2011/0301698 A1 | 12/2011 | Miller et al. |
| 2011/0301699 A1 | 12/2011 | Saadat |
| 2012/0022557 A1 | 1/2012 | Cabiri et al. |
| 2012/0022644 A1 | 1/2012 | Reich et al. |
| 2012/0059458 A1 | 4/2012 | Buchbinder et al. |
| 2012/0095455 A1 | 4/2012 | Rodmond et al. |
| 2012/0123531 A1* | 5/2012 | Tsukashima .......... A61F 2/2448 623/2.37 |
| 2012/0136436 A1 | 5/2012 | Cabiri et al. |
| 2012/0165930 A1 | 6/2012 | Gifford, III et al. |
| 2012/0245604 A1 | 9/2012 | Tegzes |
| 2012/0310330 A1 | 12/2012 | Buchbinder et al. |
| 2013/0087598 A1 | 4/2013 | Surti |
| 2013/0116780 A1 | 5/2013 | Miller et al. |
| 2013/0166022 A1 | 6/2013 | Conklin |
| 2013/0204361 A1 | 8/2013 | Adams et al. |
| 2013/0226289 A1 | 8/2013 | Shaolian et al. |
| 2013/0226290 A1 | 8/2013 | Yellin et al. |
| 2013/0282114 A1 | 10/2013 | Schweich, Jr. et al. |
| 2013/0289718 A1 | 10/2013 | Tsukashima et al. |
| 2013/0289720 A1 | 10/2013 | Dobrilovic |
| 2013/0304197 A1 | 11/2013 | Buchbinder et al. |
| 2014/0005778 A1 | 1/2014 | Buchbinder et al. |
| 2014/0046433 A1 | 2/2014 | Kovalsky |
| 2014/0058505 A1 | 2/2014 | Bielefeld |
| 2014/0114407 A1 | 4/2014 | Rajamannan |
| 2015/0173897 A1 | 6/2015 | Raanani et al. |
| 2015/0173987 A1 | 6/2015 | Albinmousa et al. |
| 2015/0351903 A1 | 12/2015 | Morriss et al. |
| 2016/0022419 A1 | 1/2016 | Yellin et al. |
| 2016/0038286 A1 | 2/2016 | Yellin et al. |
| 2016/0089235 A1 | 3/2016 | Yellin |
| 2016/0106420 A1 | 4/2016 | Foerster et al. |
| 2016/0120642 A1 | 5/2016 | Shaolian et al. |
| 2016/0120645 A1 | 5/2016 | Alon |
| 2016/0331534 A1 | 11/2016 | Buchbinder et al. |
| 2017/0042670 A1 | 2/2017 | Shaolian et al. |
| 2017/0231763 A1 | 8/2017 | Yellin |
| 2018/0042723 A1 | 2/2018 | Yellin et al. |
| 2018/0161160 A1 | 6/2018 | Shaolian et al. |
| 2018/0161161 A1 | 6/2018 | Yellin et al. |
| 2019/0083240 A1 | 3/2019 | Shaolian et al. |
| 2019/0133765 A1 | 5/2019 | Yellin et al. |
| 2021/0085463 A1 | 3/2021 | Yellin et al. |

FOREIGN PATENT DOCUMENTS

| | | |
|---|---|---|
| EP | 2600799 A | 6/2013 |
| EP | 2967700 A | 1/2016 |
| KR | 10-2004-0095482 A | 11/2004 |
| RU | 125062 U1 | 2/2013 |
| WO | 9009153 A1 | 2/1990 |
| WO | 199009153 A1 | 2/1993 |
| WO | 2003017874 A1 | 3/2003 |
| WO | 2003047467 A1 | 6/2003 |
| WO | 2005046488 A2 | 5/2005 |
| WO | 2009052427 A1 | 4/2009 |
| WO | 2009120764 A2 | 10/2009 |
| WO | 2010004546 A1 | 1/2010 |
| WO | 2010085659 A1 | 7/2010 |
| WO | 2011011443 A2 | 1/2011 |
| WO | 2011097355 A2 | 8/2011 |
| WO | 2011154942 A2 | 12/2011 |
| WO | 2012004679 A2 | 1/2012 |
| WO | 2012019052 A2 | 2/2012 |
| WO | 2012040865 A1 | 4/2012 |
| WO | 2012063228 A1 | 5/2012 |
| WO | 2012095159 A2 | 7/2012 |
| WO | 2012106354 A1 | 8/2012 |
| WO | 2012167095 A2 | 12/2012 |
| WO | 2013095816 A1 | 6/2013 |
| WO | 2013128436 A1 | 9/2013 |
| WO | 2013130641 A1 | 9/2013 |
| WO | 2013175468 A2 | 11/2013 |
| WO | 2014089424 A1 | 6/2014 |
| WO | 2014145399 A1 | 9/2014 |
| WO | 2014189509 A1 | 11/2014 |
| WO | 2014190329 A1 | 11/2014 |
| WO | 2014210600 A2 | 12/2014 |
| WO | 2015132668 A1 | 9/2015 |
| WO | 2018035118 A1 | 2/2018 |

OTHER PUBLICATIONS

International Search Report and Written Opinion for PCT/US2018/022910 dated May 23, 2018.
European Search Report in EP 17155803.4 dated Aug. 9, 2017.
International Search Report and Written Opinion for PCT/US2014/044920 dated Dec. 24, 2014.
International Search Report and Written Opinion for PCT/US2011/046659 dated Jun. 4, 2012.
International Search Report and Written Opinion for PCT/US2012/040481 dated Dec. 6, 2012.
International Search Report and Written Opinion for PCT/US2013/042275 dated Feb. 20, 2014.
International Search Report and Written Opinion for PCT/US2013/073552 dated Mar. 6, 2014.
International Search Report and Written Opinion for PCT/US2014/039545 dated Oct. 22, 2014.
International Search Report and Written Opinion for PCT/US2014/030163 dated Aug. 27, 2014.
International Search Report and Written Opinion for PCT/US2013/058102 dated Apr. 21, 2014.
International Search Report for PCT/US2013/028065 dated Jun. 27, 2013.
Lendlein et al. "Biodegradable, Elastic Shape-Memory Polymers for Potential Biomedical Applications" May 31, 2002, Science 296:1673-1676.
Supplemental European Search Report and Written Opinion for EP 12793292.9 dated Dec. 1, 2014.
Supplemental European Search Report and Written Opinion for EP 14762806.9 dated Jul. 29, 2016.
Supplementary Partial European Search Report for EP 13755441 dated Nov. 3, 2015.
International Search Report and Written Opinion for PCT/US17/46933 dated Dec. 21, 2017.
13860442.6, Extended European Search Report, dated Aug. 11, 2016, 7 pages.
19151726.7, Extended European Search Report, dated Jul. 22, 2019, 9 pages.
PCT/US2011/046659, International Search Report and Written Opinion, dated Jun. 4, 2012, 13 pages.
PCT/US2014/039454, International Search Report and Written Opinion, dated Oct. 22, 2014, 10 pages.
20209605.3, et al., Extended European Search Report, dated Mar. 9, 2021, 7 pages.
International Search Report and Written Opinion for PCT2019/064289 dated Feb. 5, 2020.

* cited by examiner

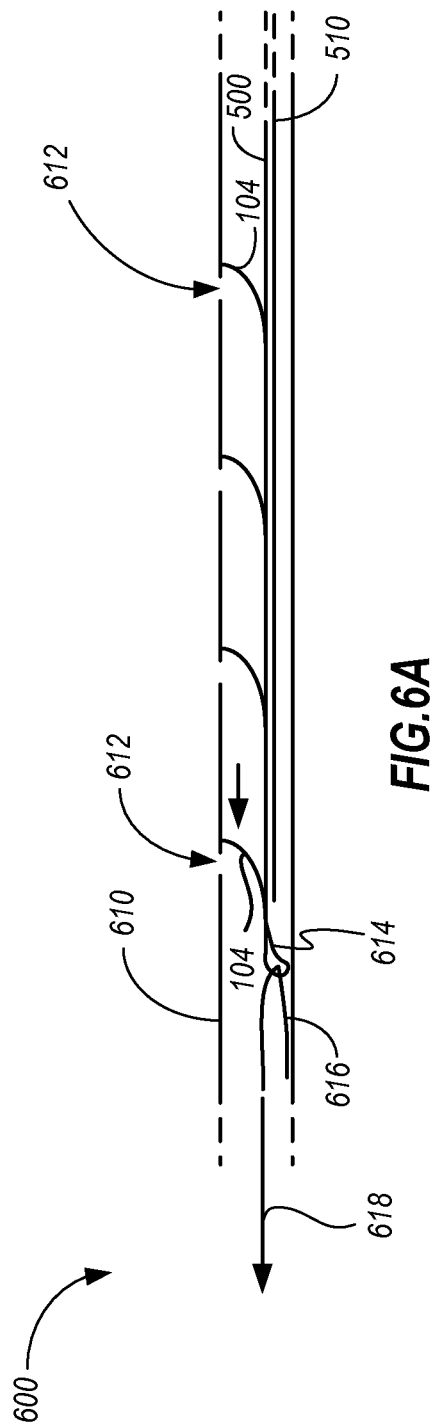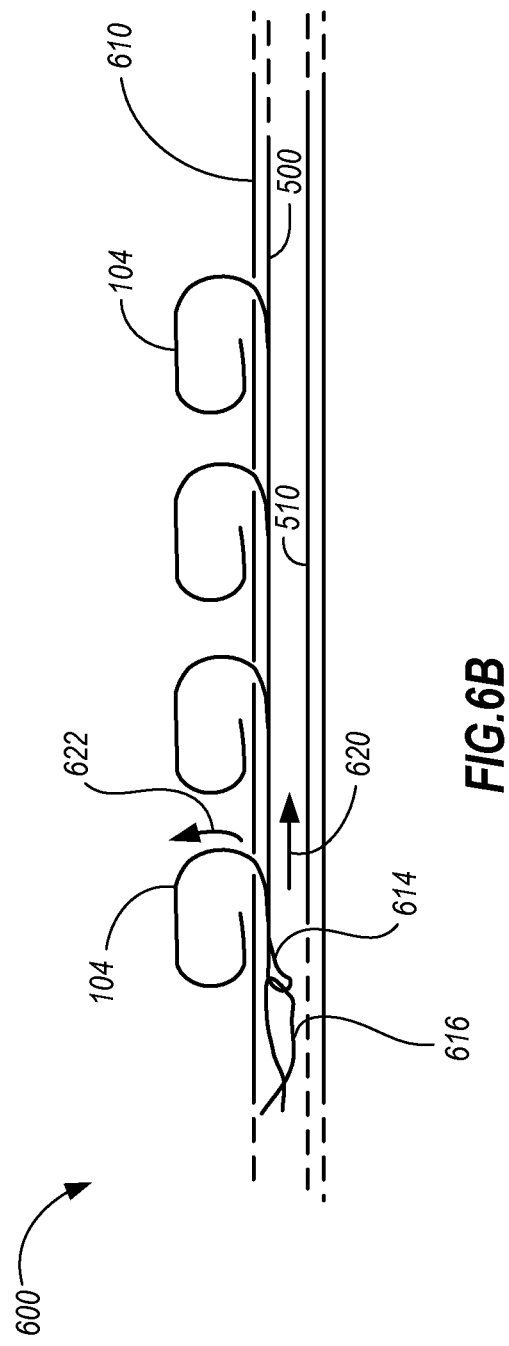

PERCUTANEOUS ANNULOPLASTY SYSTEM WITH ANTERIOR-POSTERIOR ADJUSTMENT

RELATED APPLICATIONS

The application is a divisional application of U.S. patent application Ser. No. 13/779,478, filed Feb. 27, 2013, titled "PERCUTANEOUS ANNULOPLASTY SYSTEM WITH ANTERIOR-POSTERIOR ADJUSTMENT," which claims the benefit under 35 U.S.C. § 119(e) of U.S. Provisional Patent Application No. 61/604,856, filed Feb. 29, 2012, and titled "PERCUTANEOUS ANNULOPLASTY SYSTEM WITH ANTERIOR POSTERIOR ADJUSTMENT," and of U.S. Provisional Patent Application No. 61/734,904, filed Dec. 7, 2012, and titled "ROTATIONAL BARBS," each of which is hereby incorporated herein by reference in its entirety.

TECHNICAL FIELD

The present disclosure relates to treating and repairing heart valves, and specifically to apparatus, systems, and methods for percutaneous transcatheter repair of heart valves. Disclosed embodiments include adjustable annuloplasty rings that are configured to be delivered through a catheter using, for example, a trans-septal approach, a retrograde approach, or a trans-apical approach.

BACKGROUND INFORMATION

Heart valve defects, such as regurgitation, may be caused by a relaxation of the tissue surrounding a heart valve (e.g., the mitral valve or tricuspid valve). This causes the valve opening to enlarge, which prevents the valve from sealing properly. Such heart conditions are commonly treated by a procedure during which an annuloplasty ring is fixed or secured to the annulus of the valve. Cinching or securing the tissue of the annulus to the annuloplasty ring can restore the valve opening to its approximate original size and operating efficiency.

Typically, annuloplasty rings have been implanted during open heart surgery, so that the annuloplasty ring can be sewn into the valve annulus. Open heart surgery is a highly invasive procedure that requires connecting a heart and lung machine (to pump the patient's blood and breathe for the patient), stopping the patient's heart, and cutting open the thoracic cavity and heart organ. The procedure can expose the patient to a high risk of infection and may result in a long and difficult recovery. The recovery can be particularly difficult for patients in less than optimal health due to the effects of suffering from a heart valve defect such as regurgitation.

SUMMARY OF THE DISCLOSURE

Disclosed herein are apparatus, systems, and methods for repairing heart valves through percutaneous transcatheter delivery, fixation, and adjustment of annuloplasty rings.

In one embodiment, an annuloplasty ring includes an outer hollow body member including a plurality of regions or segments. Adjacent regions or segments cooperate with one another to enable the body member to transition from an elongate insertion geometry to an annular operable geometry. The annuloplasty ring in the annular operable geometry can be expanded by an expansion tool to increase an anterior-posterior (A-P) diameter of the annuloplasty ring to an expanded state in intimate contact with tissue of a heart valve annulus. The annuloplasty ring also includes an internal anchor member located at least partially within the outer hollow member. The internal anchor member includes a plurality of anchors configured to fasten the annuloplasty ring to tissue of the heart valve annulus. The internal anchor member is configured to move the plurality of anchors with respect to a plurality of windows or gaps in the outer hollow body member to selectively deploy the plurality of anchors through the corresponding windows. The annuloplasty ring can be contracted from the expanded state to a contracted state to decrease the A-P diameter of the annuloplasty ring and decrease the A-P distance of the heart valve annulus to improve leaflet coaptation of the heart valve leaflets and reduce regurgitation through the heart valve.

In certain embodiments, methods are disclosed for percutaneous transcatheter repair of a heart valve using the adjustable annuloplasty ring.

In addition, or in other embodiments, a delivery system is disclosed for percutaneous transcatheter delivery of the adjustable annuloplasty ring.

BRIEF DESCRIPTION OF THE DRAWINGS

Understanding that drawings depict only certain embodiments and are not therefore to be considered to be limiting in nature, non-limiting and non-exhaustive embodiments of the disclosure are described and explained with additional specificity and detail through the use of the accompanying drawings.

FIGS. 6A and 6B are simplified schematics illustrating cross-section side views of an annuloplasty ring before (FIG. 6A) and after (FIG. 6B) deployment of the anchors shown in FIGS. 5A-5C according to one embodiment.

DETAILED DESCRIPTION OF PREFERRED EMBODIMENTS

The present disclosure provides systems and methods for repairing heart valves through percutaneous transcatheter delivery and fixation of annuloplasty rings to heart valves. The embodiments of annuloplasty rings can be configured in both an elongate insertion geometry that can be inserted into a catheter tube and an operable geometry providing a curved and rigid or semi-rigid annular shape.

In certain embodiments, an annuloplasty ring in the operable geometry can be expanded to an expanded state using an expansion tool. The expansion of the annuloplasty ring to the expanded state increases an anterior-posterior (A-P) diameter of the annuloplasty ring to position the annuloplasty ring in abutment with tissue of an annulus of a target heart valve that is to be repaired. Following fixation of the annuloplasty ring to the annulus, the annuloplasty ring can be contracted from the expanded state to a contracted state to decrease the A-P diameter of the annuloplasty ring and decrease the A-P distance of the heart valve annulus, and thereby improve leaflet coaptation of the heart valve leaflets and reduce regurgitation through the heart valve.

In certain embodiments, an annuloplasty ring is delivered percutaneously to the mitral and/or tricuspid valve annulus of the heart. The disclosed embodiments apply, for example, to trans-septal, retrograde, or trans-apical approaches for delivering annuloplasty rings to an annulus of a heart valve. For delivery of annuloplasty rings into the mitral valve, percutaneous delivery may involve a retrograde approach from the femoral artery, an antegrade approach via a trans-septal entry, or a trans-apical approach through the base or apex of the heart through the left ventricle to the left atrium. Delivery of annuloplasty rings to the tricuspid valve may include an approach from the inferior or superior vena cava.

Certain annuloplasty rings disclosed herein are small and flexible enough to be percutaneously delivered, but can be put into a rigid or semi-rigid ring shape and then securely anchored into the heart valve annulus without having to open up the chest. Disclosed embodiments include annuloplasty rings, delivery systems, and methods for anchoring the annuloplasty ring around the valve annulus and then adjusting an A-P distance of the annuloplasty ring.

Example Ring Embodiments with Biasing Elements

Figure 1A:
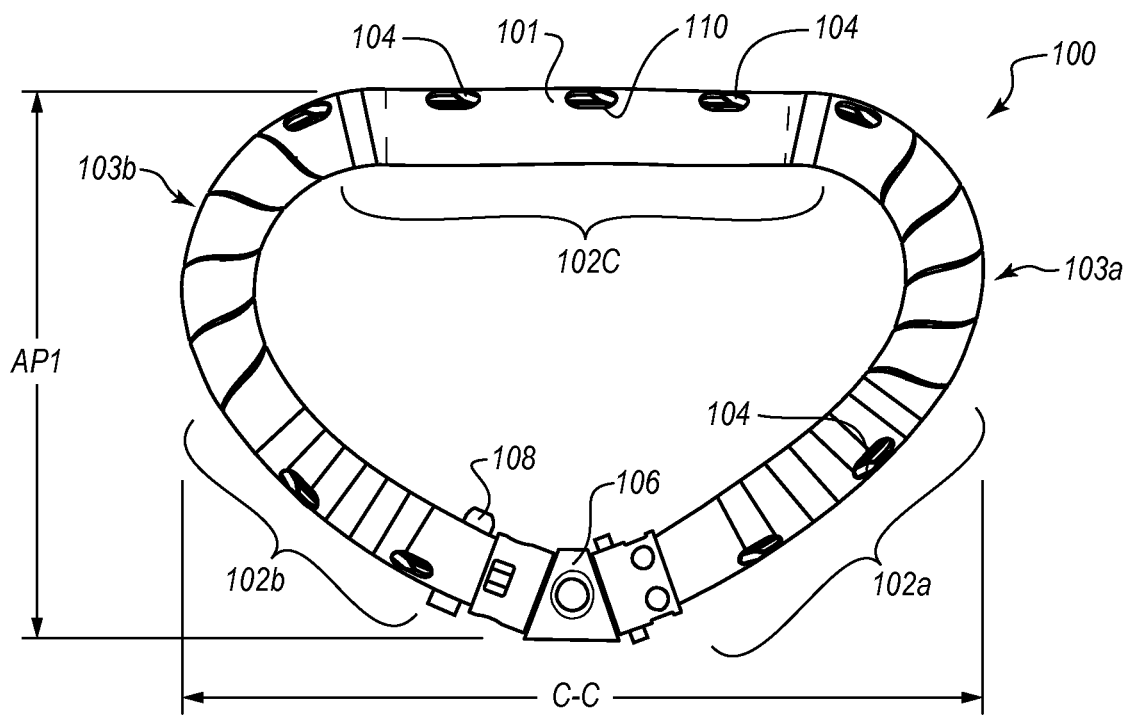
FIG. 1A is a perspective view of an adjustable annuloplasty ring according to one embodiment. The annuloplasty ring is in an annular (D-shaped) operable geometry and a contracted state.
Figure 1B:
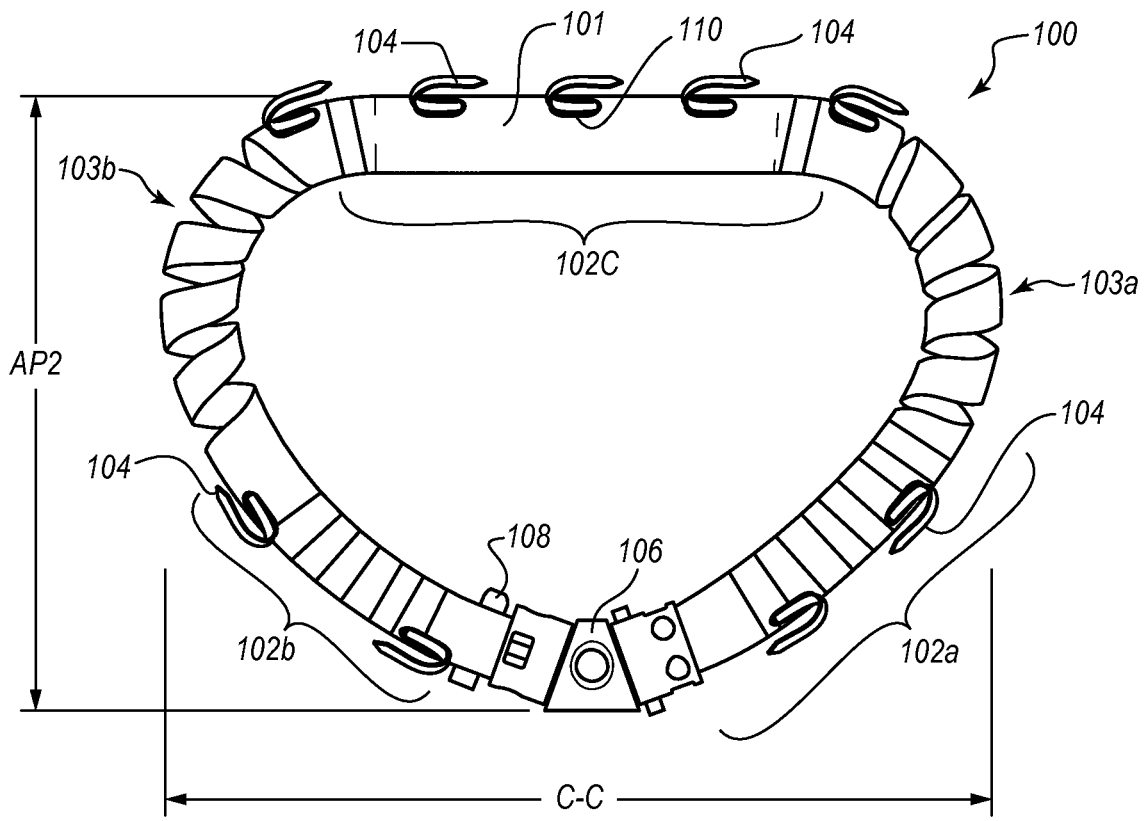
FIG. 1B is a perspective view of the adjustable annuloplasty ring of FIG. 1A in an expanded state.

FIG. 1A is a simplified schematic diagram illustrating a perspective view of an adjustable annuloplasty ring 100 according to one embodiment. The annuloplasty ring 100 illustrated in FIG. 1A is in an annular (D-shaped) operable geometry in a contracted state. FIG. 1B is a simplified schematic diagram illustrating a perspective view of the adjustable annuloplasty ring 100 of FIG. 1A in an expanded state. The annuloplasty ring 100 is configured to enable percutaneous, transcatheter annuloplasty to repair a heart valve. The annuloplasty ring 100 may be fastened, percutaneously, to the annulus of the heart valve while in the expanded state and then reduced to the contracted state to decrease an A-P distance of the target valve and thereby improve leaflet coaptation of the target valve and reduce regurgitation through the target valve.

Referring collectively to FIGS. 1A and 1B, the annuloplasty ring 100 includes a body member 101 having a plurality of regions 102a, 102b, 102c (collectively 102), biasing elements 103a, 103b (collectively 103), a plurality of anchors 104, a ring closure lock 106, and a pivot 108. In FIGS. 1A and 1B, as well as in other embodiments disclosed herein, the body member 101, including the plurality of regions 102, is arranged in a "D-shape" in the operable geometry. The D-shaped annuloplasty ring 100 has a certain geometrical ratio that is in conformance (or approximate conformance) with the anatomical geometry of the human mitral valve annulus. For example, in certain embodiments the ratio of the A-P distance to the commissure-commissure (C-C) distance of the annuloplasty ring 100 when implanted (i.e., in the contracted state) is in a range between about 0.60 and about 0.70. In one embodiment, the implanted ratio of the A-P distance to the C-C distance is about 0.62.

Although the illustrated embodiment of an annuloplasty ring 100 of FIGS. 1A and 1B is a D-shaped operable geometry, artisans will recognize from the disclosure herein that other annular-shaped operable geometries may also be used. For example, circular or oval operable geometries may be used.

The body member 101 may include a hollow hypotube (or outer hollow member). The hypotube may be cut from, for example, a tube to form the plurality of regions 102. The cuts may define a shape and/or characteristics of the body member 101. For example, the laser cuts may define the plurality of regions 102 (and define how the plurality of regions 102 interact), anchor windows 110, and/or the biasing elements 103.

In certain embodiments, the body member 101 may include a shape memory (e.g., Nitinol) hypotube into which a plurality of cuts and/or segments may be laser cut to define a size, shape, and/or characteristics of the plurality of regions 102. The shape memory hypotube may be heat set to a "memorized" annular shape (e.g., the D-shaped operable geometry). The shape memory hypotube may be superelastic such that applying sufficient stress may place the body member 101, including the plurality of regions 102, into the elongate insertion geometry and releasing the stress allows the body member 101, including the plurality of regions 102, to resume the D-shaped operable geometry.

In addition to the operable geometry shown in FIGS. 1A and 1B, the body member 101 is transitionable from an elongate insertion geometry (see, e.g., FIG. 9A) to the annular operable geometry shown in FIGS. 1A and 1B. The elongate insertion geometry allows the annuloplasty ring 100 to be inserted into and passed through a catheter for percutaneous passage of the annuloplasty ring 100 into the heart of a patient. A transition from an elongate insertion geometry to an annular operable geometry is illustrated in FIGS. 9A-9D, and discussed below with reference to the same.

Once in an annular operable geometry as shown in FIGS. 1A and 1B, the annuloplasty ring 100 has a contracted state as shown in FIG. 1A and an expanded state as shown in FIG. 1B. The biasing elements 103 are configured to be expanded to increase the A-P distance of the annuloplasty ring 100 to an expanded state. The A-P distance AP1 of the contracted state of FIG. 1A is enlarged a distance d such that the A-P distance AP2 of the expanded state FIG. 1B is larger (AP2=AP1+d). Expansion of the biasing elements 103 allows the body member 101 to be expanded to an expanded state. In situ in the heart, expansion of the body member 101 to the expanded state may enlarge the annuloplasty ring 100 to a size conforming, or approximately conforming, to an annulus of a target heart valve to be repaired. Expansion of the body member 101 may be accomplished by an expansion tool, such as a balloon, a cage, or another tool as shown in FIGS. 10, 11, 12A-12B, 13A-13B, and 14A-14B, and described below with reference to the same. In the illustrated embodiment of FIGS. 1A and 1B, a biasing element 103a disposed between a first posterior region 102a and an anterior region 102c and a biasing element 103b disposed between a second posterior region 102b and the anterior region 102c enable a desired expansion from the contracted state shown in FIG. 1A to the expanded state shown in FIG. 1B.

The expanded state of FIG. 1B may be such that the annuloplasty ring 100 is disposed in abutment with, or in intimate contact with, the annulus of the target valve. Disposing the annuloplasty ring 100 in intimate contact with the annulus enhances an anchoring process in which the plurality of anchors 104 is deployed to fasten the annuloplasty ring 100 to the annulus. Once the annuloplasty ring 100 is fastened to the annulus, the annuloplasty ring 100 can be contracted from the expanded state of FIG. 1B back to the contracted state of FIG. 1A to reduce a diameter of the annulus of the target valve.

Contraction of the annuloplasty ring 100 from the expanded state to the contracted state decreases the A-P distance of the annuloplasty ring 100 and, with the plurality of anchors 104 securing the annuloplasty ring 100 to the annulus, also decreases an A-P distance of the target valve to improve leaflet coaptation and reduce regurgitation through the target valve. In the illustrated embodiment of FIGS. 1A and 1B, contraction of the annuloplasty ring 100 from the expanded state to the contracted state is accomplished by the biasing elements 103. The biasing elements 103 may bias the annuloplasty ring 100 toward the contracted state such that expansion of the annuloplasty ring 100 to the expanded state stores potential energy in the biasing elements 103. Releasing the biasing elements 103 (e.g., releasing or otherwise removing an expansion tool and/or expansion force) releases the stored potential energy and thereby forces movement of the first posterior region 102a and the second posterior region 102b of the body member 101 toward the anterior region 102c of the body member 101 to decrease the A-P distance of the annuloplasty ring 100 to the contracted state. In other words, the biasing elements 103, upon release, actively transition the annuloplasty ring 100 from the expanded state to the contracted state.

A typical range for change of the A-P distance d (between the expanded state and the contracted state) is between 3 mm and 5 mm. The range of d may depend on the overall size of the annuloplasty ring 100. For example, for a final geometry of the annuloplasty ring 100 that is 26 mm, a change distance d of about 3 mm may be desired. As another example, for a final geometry of the annuloplasty ring 100 that is 36 mm, a change distance d of about 5 mm may be desired.

The biasing elements 103 of the illustrated annuloplasty ring 100 of FIGS. 1A and 1B may be a spiral cut or helical portion of the body member 101 that is laser cut into the body member 101. The spiral cut or helical portion, because it is cut into the body member 101, is a biasing element 103 that is integral to the body member 101. The spiral cut portion of the body member 101, as shown in FIG. 1B, may form or otherwise define a spiral shape configured to expand to allow the anterior region 102c to move away from the first posterior region 102a and from the second posterior region 102b, thereby increasing the A-P distance of the annuloplasty ring 100. Also, the spiral cut or helical portion of the body member 101 may be biased toward a relaxed position, or the contracted state as shown in FIG. 1A, such that expansion of the spiral cut or helical portion stores potential energy and release of an expansion force results in a release of potential energy and contraction toward the contracted state.

Other integral biasing elements 103 may be utilized. For example, a diamond cut pattern cut into the body member 101 may allow desired expansion and biasing toward the contracted state. In another embodiment, a corrugated pattern (e.g., folds) may be formed in the body member 101. The corrugated pattern may allow desired expansion to increase the A-P distance of the annuloplasty ring 100 and may be biased toward the contracted state.

Figure 2A:
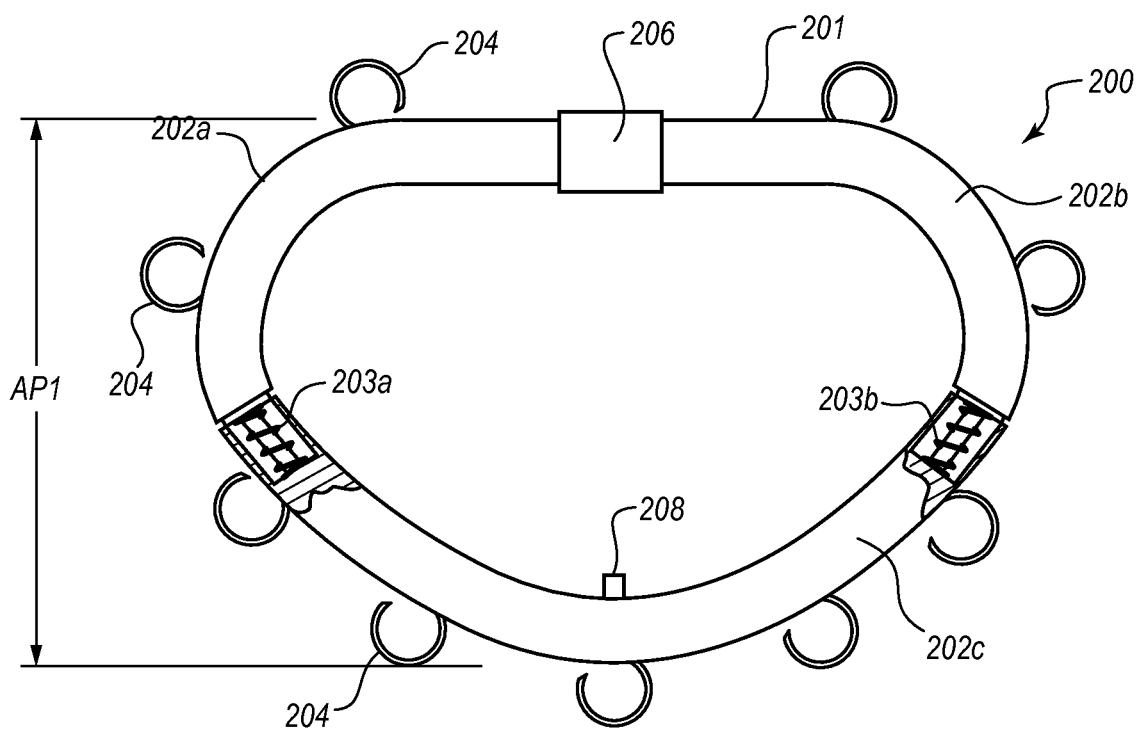
FIG. 2A is a simplified schematic diagram illustrating a perspective view of an adjustable annuloplasty ring according to another embodiment. The annuloplasty ring is in an annular (D-shaped) operable geometry and a contracted state.
Figure 2B:
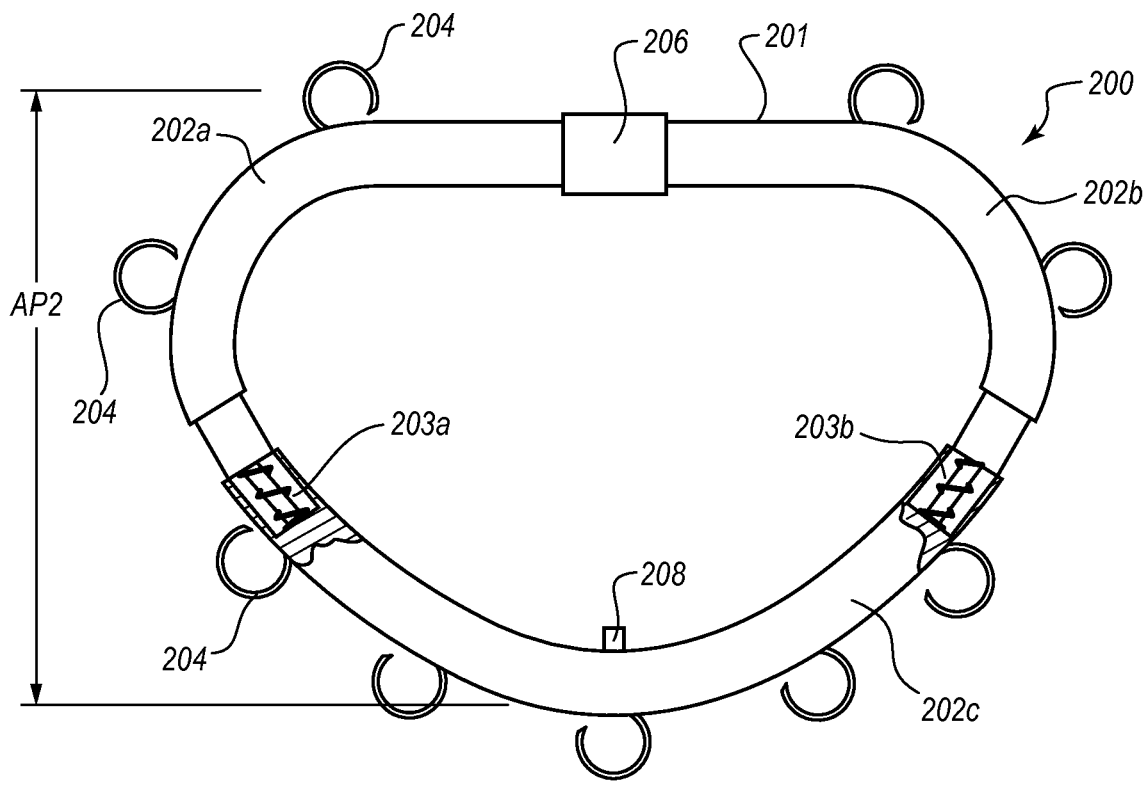
FIG. 2B is a simplified schematic diagram illustrating a perspective view of the adjustable annuloplasty ring of FIG. 2A in an expanded state.

In addition to integral biasing elements 103 (formed integrally in the body member 101 of the annuloplasty ring 100), other biasing elements 103 may be used that are not integral to the body member 101. For example, FIGS. 2A and 2B illustrate an embodiment in which the biasing element 103 is a spring and which is not integral to the body member 101, as discussed below with reference to the same figures. In still other embodiments, the biasing element 103 may comprise a nonintegral biasing component (e.g., a spring) to complement or enhance operation of an integrally formed biasing element.

The plurality of anchors 104, as noted above, is configured to secure the annuloplasty ring 100 to the annulus of the heart valve. In certain embodiments, the anchors 104 are sufficient such that additional suturing of the annuloplasty ring 100 to the valve annulus is not needed. In FIG. 1A the anchors 104 are within the body member 101 in an insertion geometry. In FIG. 1B, the anchors 104 are curved in the illustrated deployed configuration. The anchors 104 in other embodiments may include other shapes, such as linear or helical deployed configurations. In certain embodiments, the anchors 104 include a shape memory material (e.g., Nitinol) that is heat set to a deployed configuration (e.g., curved configuration, linear configuration, or helical configuration). Artisans will recognize from the disclosure herein that combinations of different deployed anchor configurations may also be used.

The anchors 104 are superelastic such that applying sufficient stress places the anchors 104 into an introduction configuration and releasing the stress allows the anchors 104 to resume their respective deployed configurations. In certain embodiments, the anchors 104 lay flat against the body member 101 in the introduction configuration during insertion of the annuloplasty ring 100 through the catheter. As discussed below, in other embodiments, the anchors 104 are retracted inside the hollow body member 101 of the annuloplasty ring 100 in the introduction configuration during insertion of the annuloplasty ring 100 through the catheter. In such embodiments, the anchors 104 may be selectively deployed at a desired time (e.g., after the annuloplasty ring 100 is properly positioned against, or in abutment with, the annulus of the heart valve). In certain embodiments, the superelastic property of the anchors 104 is used to self-propel the anchors 104 into the annulus of the heart valve. The anchors 104 may be configured to be deployed from within the body member 101 through anchor windows 110 in the body window.

Figure 15A:
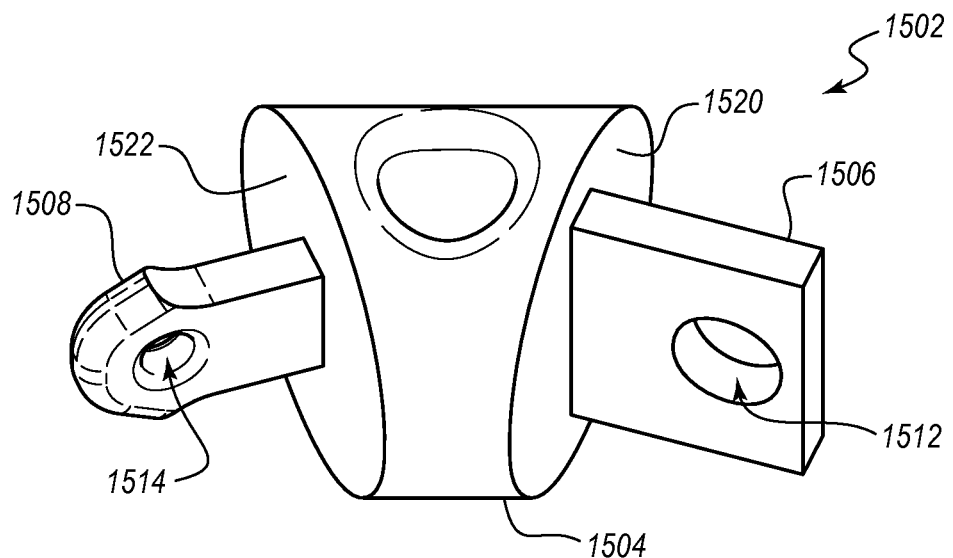
FIG. 15A is a perspective view of an angled snap of a ring closure lock according to one embodiment.
Figure 15B:
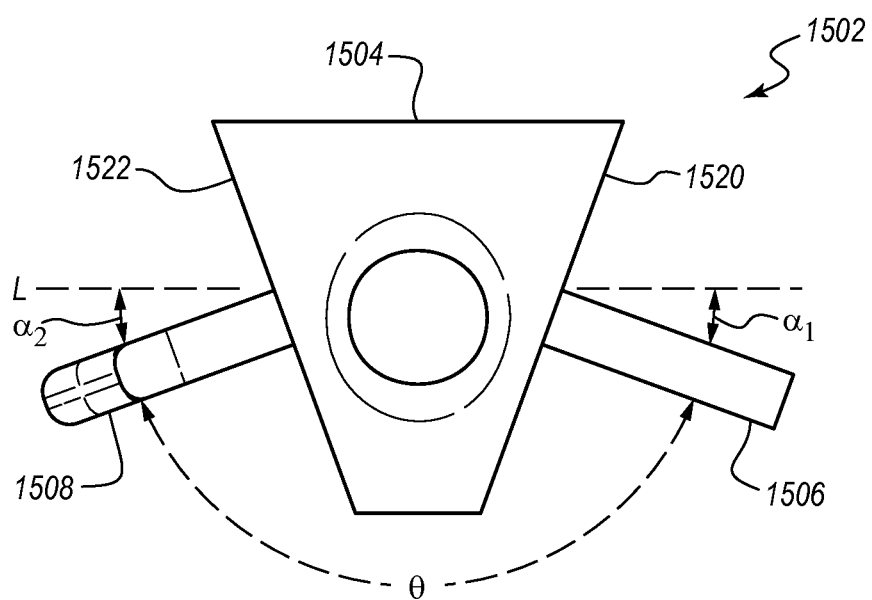
FIG. 15B is a top view of the angled snap of the ring closure lock of FIG. 15A.

The ring closure lock 106 is used to secure two open ends of the annuloplasty ring 100 to form a closed ring of the operable geometry. In certain embodiments, the ring closure lock 106 includes a female snap and a male snap. As discussed in greater detail below, the annuloplasty ring 100 may be "snap locked" using wires or sutures to pull a male snap into a female snap. The ring closure lock 106 of the illustrated annuloplasty ring 100 of FIGS. 1A and 1B is disposed at a posterior side of the annuloplasty ring 100. The ring closure lock 106 allows an angled coupling of the two ends, for example at an apex of a curved side of a D-shaped annular operable geometry. A bent or angled ring closure lock 106, according to one embodiment, is shown in FIGS. 15A-15B, and discussed in greater detail below with reference to the same.

The pivot 108 is used to automatically rotate the annuloplasty ring 100 after it exits the catheter within the heart to align the plane of the annuloplasty ring 100 (in the annular operable geometry) with the plane of the heart valve. The annuloplasty ring 100 is pushed from the catheter in a direction that is substantially perpendicular to the plane of the heart valve (e.g., parallel to the general direction of blood flow through the valve). Upon exiting the catheter, the annuloplasty ring 100 is rotated at or about the pivot 108 to allow proper positioning of the annuloplasty ring 100 against the annulus. With the annuloplasty ring 100 properly oriented in alignment with the plane of the heart valve, the annuloplasty ring 100 can be expanded to the expanded state. For example, an expansion tool can be used to expand the annuloplasty ring 100, as shown in FIGS. 10, 11, 12A-12B, 13A-13B, and 14A-14B, and discussed below with reference to the same. The annuloplasty ring 100 in the expanded state can be pressed against the valve annulus before deploying the anchors 104, and an act of deploying the anchors 104 drives the anchors 104 into the tissue. A positioning tool may facilitate expansion and/or proper positioning/orientation of the annuloplasty ring 100 against the heart valve annulus. An intimate contact tool, such as a tri-pod tool or a bi-pod tool, shown for example in FIGS. 12A-12B, 13A-13B, and 14A-14B, and discussed below with reference to the same, may be used to position the annuloplasty ring 100 in abutment against the annulus of the target heart valve, or otherwise in intimate contact with the annulus of the target heart valve. In addition, fluoroscopy, ultrasound, and/or other imaging techniques may be used to assist in proper positioning of the annuloplasty ring 100 against the heart valve annulus.

Although not shown in FIGS. 1A and 1B, certain ring embodiments may include a selectively adjustable member for changing the size and/or shape of the annuloplasty ring 100 postoperatively to compensate for changes in the size of the heart and/or the treated heart valve. Examples of a selectively adjustable member are provided in U.S. patent application Ser. No. 13/198,582, filed Aug. 4, 2011, and titled PERCUTANEOUS TRANSCATHETER REPAIR OF HEART VALVES, which is hereby incorporated herein by reference in its entirety.

Figure 1C:
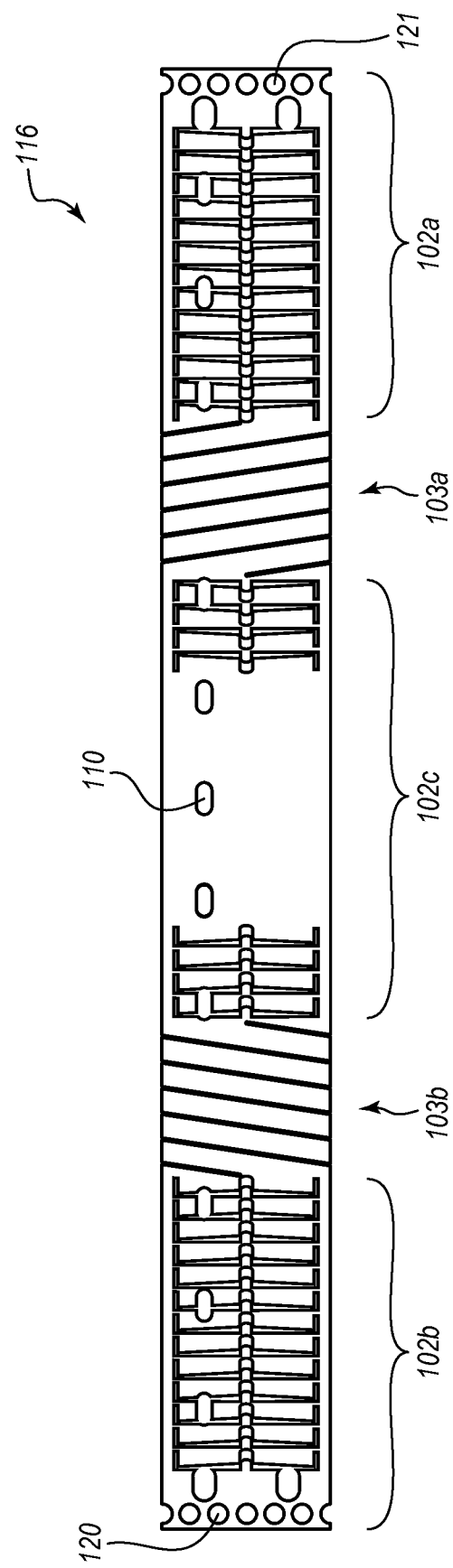
FIG. 1C is a schematic diagram illustrating a cutting pattern used for laser processing a hypotube of the adjustable annuloplasty ring shown in FIGS. 1A and 1B.

FIG. 1C is a schematic diagram illustrating a cutting pattern 116 used for laser processing a hypotube to form the body member 101 of the adjustable annuloplasty ring 100 shown in FIGS. 1A and 1B. The pattern 116 enables a hypotube or outer tube (also referred to herein as an "outer hollow member") to be cut for use as a body member 101 of an annuloplasty ring 100 according to one embodiment. The cutting pattern 116 corresponds to the entire body member 101 as if the body member 101 were cut along a longitudinal axis and unrolled. The cutting pattern 116 enables cutting the hypotube to form the plurality of regions 102 and the integral biasing elements 103. The cutting pattern 116 shown in FIG. 1C defines the configuration of the plurality of regions 102 and how the regions 102 interact with adjacent regions as the body member 101 transitions from the elongate insertion geometry shown to the annular operable geometry.

The cutting pattern 116 also enables cutting the hypotube to form one or more through holes 120, 121 at each end to allow one or more pins (not shown) to couple male and/or female components of the ring closure lock 106 to respective ends of the body member 101. The cutting pattern 116 may also enable cutting the hypotube to form anchor windows 110 through which the plurality of anchors 104 are deployed.

FIG. 2A is a simplified schematic diagram illustrating a perspective view of an adjustable annuloplasty ring 200 according to another embodiment. The annuloplasty ring 200 is in an annular (D-shaped) operable geometry and a contracted state. FIG. 2B is a simplified schematic diagram illustrating a perspective view of the adjustable annuloplasty ring 200 of FIG. 2A in an expanded state. The annuloplasty ring 200 is configured to enable percutaneous, transcatheter annuloplasty to repair a heart valve.

Referring collectively to FIGS. 2A and 2B, the annuloplasty ring 200 includes a body member 201 having a plurality of regions 202a, 202b, 202c (collectively 202), biasing elements 203a, 203b (collectively 203), a plurality of anchors 204, a ring closure lock 206, and a pivot 208. The body member 201 is a "D-shape" in the operable geometry, but artisans will recognize from the disclosure herein that other annular-shaped operable geometries may also be used. For example, circular or oval operable geometries may be used. Different from the annuloplasty ring 100 of FIGS. 1A-1B, the ring closure lock 206 is disposed on the anterior side of the annuloplasty ring 200 (rather than the posterior side).

In addition to the operable geometry shown in FIGS. 2A and 2B, the body member 201 is transitionable from an elongate insertion geometry (see, e.g., FIG. 9A) to the annular operable geometry shown in FIGS. 2A and 2B. The elongate insertion geometry allows the annuloplasty ring 200 to be inserted into and passed through a catheter for percutaneous passage of the annuloplasty ring 200 into the heart of a patient. A transition from an elongate insertion geometry to an annular operable geometry is illustrated in FIGS. 9A-9D, and discussed below with reference to the same.

Once in an annular operable geometry, the annuloplasty ring 200 has a contracted state as shown in FIG. 2A and an expanded state as shown in FIG. 2B. The biasing elements 203 are configured to allow expansion of the body member 201 to increase the A-P distance of the annuloplasty ring 200 to an expanded state. In situ within the heart, expansion of the body member 201 to the expanded state may enlarge the annuloplasty ring 200 to a size conforming, or approximately conforming, to an annulus of a target heart valve to be repaired. Expansion of the body member 201 may be accomplished by an expansion tool, such as a balloon, a cage, or another expansion tool as shown in FIGS. 10, 11, 12A-12B, 13A-13B, and 14A-14B, and described below with reference to the same. In the illustrated embodiment of FIGS. 2A and 2B, a biasing element 203a disposed between a first anterior region 202a and a posterior region 202c and a biasing element 203b disposed between a second anterior region 202b and the posterior region 202c enable a desired expansion from the contracted state shown in FIG. 2A to the expanded state shown in FIG. 2B.

The expanded state of FIG. 2B may be such that the annuloplasty ring 200 is disposed in abutment with, or in intimate contact with, the annulus of the target valve. Disposing the annuloplasty ring 200 in intimate contact with the annulus enhances an anchoring process in which the plurality of anchors 204 is deployed to fasten the annuloplasty ring 200 to the annulus.

Once the annuloplasty ring 200 is fastened to the annulus, the annuloplasty ring 200 can be contracted from the expanded state of FIG. 2B back to the contracted state of FIG. 2A to reduce a diameter of the annulus of the target valve. Contraction of the annuloplasty ring 200 may include the first and second anterior regions 202a, 202b of the body member 201 moving in a telescopic manner into the posterior region 202c as the biasing members 203 force movement of the first and second anterior regions 202a, 202b of the body member 201 toward the posterior region 202c. Contraction of the annuloplasty ring 200 from the expanded state to the contracted state decreases the A-P distance of the annuloplasty ring 200 and, with the plurality of anchors 204 securing the annuloplasty ring 200 to the annulus, also decreases the A-P distance of the target valve to improve leaflet coaptation and reduce regurgitation through the target valve.

In the illustrated embodiment of FIGS. 2A and 2B, contraction of the annuloplasty ring 200 from the expanded state to the contracted state is accomplished by the biasing elements 203. The biasing elements 203 may bias the annuloplasty ring 200 toward the contracted state such that expansion of the annuloplasty ring 200 to the expanded state stores potential energy in the biasing elements 203. Releasing the biasing elements 203 (e.g., releasing or otherwise removing an expansion tool and/or expansion force) releases the stored potential energy and thereby forces movement of the first anterior region 202a and the second anterior region 202b of the body member 201 toward the anterior region 202c of the body member 201 to decrease the A-P distance of the annuloplasty ring 200 to the contracted state. In other words, the biasing elements 203, upon release, actively transition the annuloplasty ring 200 from an expanded state to the contracted state.

The biasing elements 203 of the illustrated annuloplasty ring 200 of FIGS. 2A and 2B may include springs or another similar element that is nonintegral to the body member. The springs of the biasing elements 203 allow the anterior regions 202a, 202b to move away from the first posterior region 202c, thereby increasing the A-P distance of the annuloplasty ring 200.

The A-P distance AP1 of the contracted state of FIG. 2A is enlarged a distance d upon expansion of the annuloplasty ring 200 such that the A-P distance AP2 of the expanded state FIG. 2B is larger (AP2=AP1+d). The springs of the biasing elements 203 may be biased toward a relaxed position, or the contracted state as shown in FIG. 2A, such that expansion of the springs stores potential energy and release of the springs results in a release of potential energy and contraction toward the contracted state.

The plurality of anchors 204 are configured to secure the annuloplasty ring 200 to the annulus of the heart valve. In FIGS. 2A and 2B, the anchors 204 are curved in the illustrated deployed configuration. The anchors 204 in other embodiments may include other shapes, such as linear or helical deployed configurations. In certain embodiments, the anchors 204 include a shape memory material (e.g., Nitinol) that is heat set to a deployed configuration (e.g., curved configuration, linear configuration, or helical configuration). Artisans will recognize from the disclosure herein that combinations of different deployed anchor configurations may also be used.

The anchors 204 may be superelastic such that applying sufficient stress places the anchors 204 into an introduction configuration and releasing the stress allows the anchors 204 to resume their respective deployed configurations. In certain embodiments, the anchors 204 lay flat against the body member 201 in the introduction configuration during insertion of the annuloplasty ring 200 through the catheter. As discussed below, in other embodiments, the anchors 204 are retracted inside a hollow body member 201 of the annuloplasty ring 200 in the introduction configuration during insertion of the annuloplasty ring 200 through the catheter. In such embodiments, the anchors 204 may be selectively deployed at a desired time (e.g., after the annuloplasty ring 200 is properly positioned against, or in abutment with, the annulus of the heart valve). In certain embodiments, the superelastic property of the anchors 204 is used to self-propel the anchors 204 into the annulus of the heart valve.

The ring closure lock 206 is used to secure two open ends of the annuloplasty ring 200 to form a closed ring of the operable geometry. Different from the annuloplasty ring 100 of FIGS. 1A-1B, the ring closure lock 206 is disposed on the anterior side of the annuloplasty ring 200 (rather than the posterior side). In certain embodiments, the ring closure lock 206 includes a female snap and a male snap. The annuloplasty ring 100 may be "snap locked" using wires or sutures to pull a male snap into a female snap.

The pivot 208 facilitates rotation of the annuloplasty ring 200 after it exits the catheter within the heart to align the plane of the annuloplasty ring 200 (in the annular operable geometry) with the plane of the heart valve, as previously described.

Figure 3A:
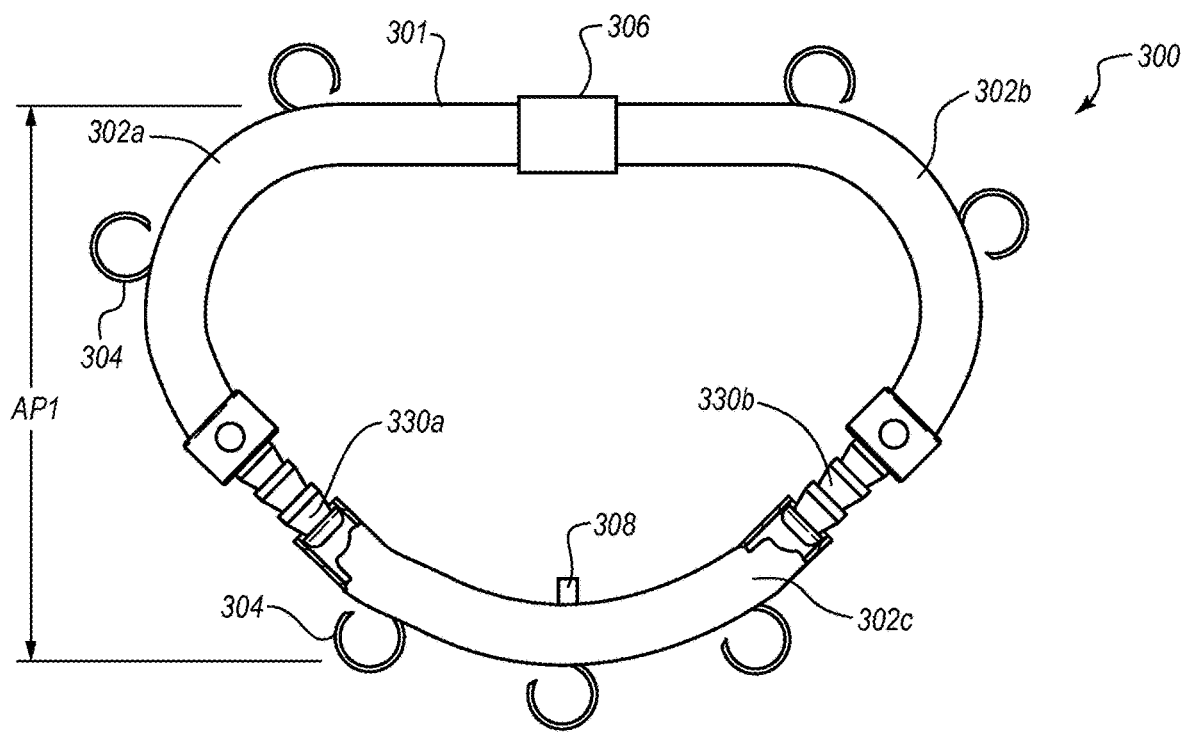
FIG. 3A is a simplified schematic diagram illustrating a perspective view of an adjustable annuloplasty ring according to another embodiment. The annuloplasty ring is in an annular (D-shaped) operable geometry and in an expanded state.
Figure 3B:
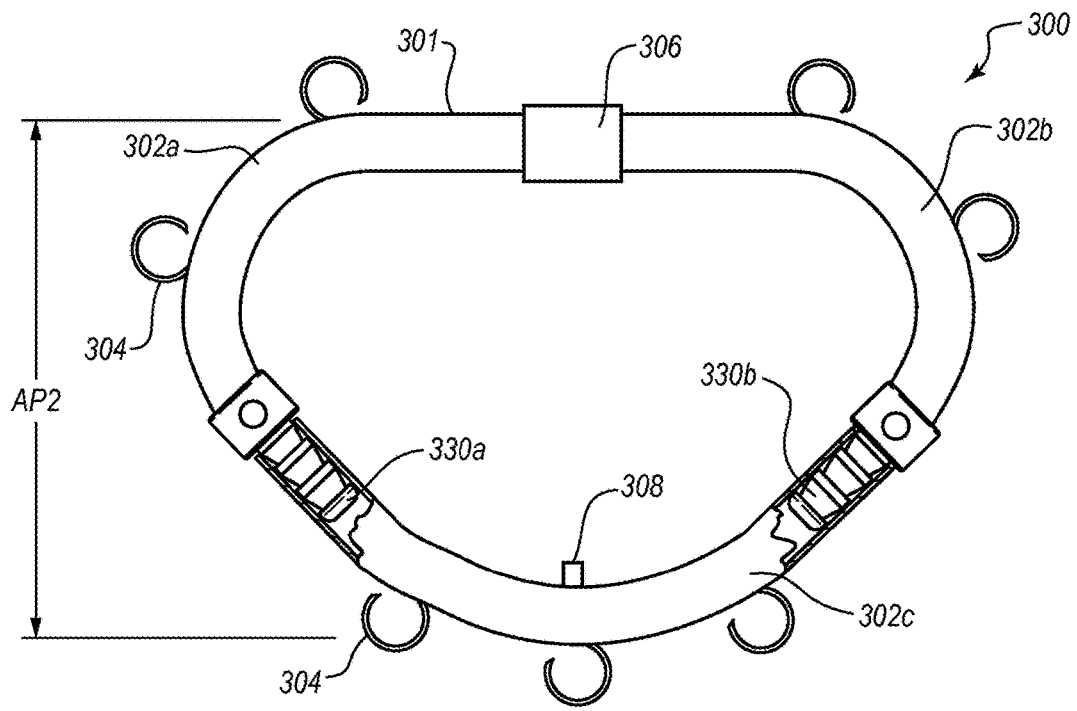
FIG. 3B is a simplified schematic diagram illustrating a perspective view of the adjustable annuloplasty ring of FIG. 3A in a contracted state.

FIG. 3A is a simplified schematic diagram illustrating a perspective view of an adjustable annuloplasty ring 300 according to another embodiment. The annuloplasty ring 300 is in an annular (D-shaped) operable geometry and an expanded state. FIG. 3B is a simplified schematic diagram illustrating a perspective view of the adjustable annuloplasty ring 300 of FIG. 3A in a contracted state. The annuloplasty ring 300 is configured to enable percutaneous, transcatheter annuloplasty to repair a heart valve.

Referring collectively to FIGS. 3A and 3B, the annuloplasty ring 300 includes a body member 301 having a plurality of regions 302a, 302b, 302c (collectively 302), a plurality of anchors 304, a ring closure lock 306, and a pivot 308, similar to previously described embodiments. The annuloplasty ring 300 is transitionable from an elongate insertion geometry (see, e.g., FIG. 9A) to the annular operable geometry shown in FIGS. 3A and 3B. The elongate insertion geometry allows the annuloplasty ring 300 to be inserted into and passed through a catheter for percutaneous passage of the annuloplasty ring 300 into the heart of a patient, as illustrated in FIGS. 9A-9D, and discussed below with reference to the same.

The plurality of regions 302 of the illustrated annuloplasty ring 300 of FIGS. 3A and 3B may be separate, individual segments. The segments 302 may be coupled together by stepped connectors 330a, 330b (collectively 330) in the annular operable geometry. The stepped connectors 330 are configured to enable the body member 301 to be adjustable to decrease the A-P distance of the annuloplasty ring 300 from an expanded state as shown in FIG. 3A to a contracted state as shown in FIG. 3B. The stepped connectors 330 initially couple the posterior segment 302c to each of a first anterior segment 302a and a second anterior segment 302b in the expanded state of FIG. 3A, conforming, or approximately conforming, to an annulus of a target heart valve to be repaired. The expanded state of FIG. 3A may be such that the annuloplasty ring 300 is disposed in abutment with, or in intimate contact with, the annulus of the target valve, thereby enhancing an anchoring process in which the plurality of anchors 304 are deployed to fasten the annuloplasty ring 300 to the annulus.

Once the annuloplasty ring 300 is fastened to the annulus, the annuloplasty ring 300 can be contracted from the expanded state of FIG. 3A to the contracted state of FIG. 3B to reduce a diameter of the annulus of the target valve. Contraction of the annuloplasty ring 300 may include the stepped connectors 330 moving in a telescopic manner into the posterior region 302c as the first and second anterior regions 302a, 302b of the body member 301 move toward the posterior region 302c. Contraction of the annuloplasty ring 300 from the expanded state to the contracted state decreases the A-P distance of the annuloplasty ring 300 and, with the plurality of anchors 304 securing the annuloplasty ring 300 to the annulus, also decreases an A-P distance of the target valve to improve leaflet coaptation and reduce regurgitation through the target valve. The stepped connectors 330 allow for multiple degrees of adjustment. For example a stepped connector having two engagement steps (see engagement steps 402 in FIGS. 4A and 4B) may allow two degrees of adjustment, as discussed more fully below.

In the illustrated embodiment of FIGS. 3A and 3B, contraction of the annuloplasty ring 300 from the expanded state to the contracted state may be accomplished percutaneously through use of sutures or wires to force the posterior segment 302c toward the first and second anterior segments 302a, 302b and vice versa.

In certain embodiments, a biasing element (not shown in FIGS. 3A and 3B) may bias the annuloplasty ring 300 toward the contracted state and aid in contraction of the annuloplasty ring 300 from the expanded state to the contracted state. In other embodiments, a biasing element may enable expansion from an initial state to an expanded state and a stepped connector 330 may operate to ensure expansion from the contracted state is restricted.

Different from the embodiments of FIGS. 1A-1C and 2A and 2B, the annuloplasty ring 300 of FIGS. 3A and 3B is initially in an expanded state upon transition to the annular operable geometry. In other words, the initial A-P distance AP1 of the annuloplasty ring 300 is sufficient to conform or substantially conform to the A-P distance of a target valve. The A-P distance AP1 of the expanded state of FIG. 3A is decreased a distance d upon contraction of the annuloplasty ring 300 such that the A-P distance AP2 of the contracted state FIG. 3B is smaller (AP2=AP1−d). The decrease of the A-P distance, with the anchors fastening the annuloplasty ring 300 to the annulus of the valve, decreases the A-P distance of the target valve to improve leaflet coaptation of the target valve and reduce regurgitation through the target valve.

Figure 4A:
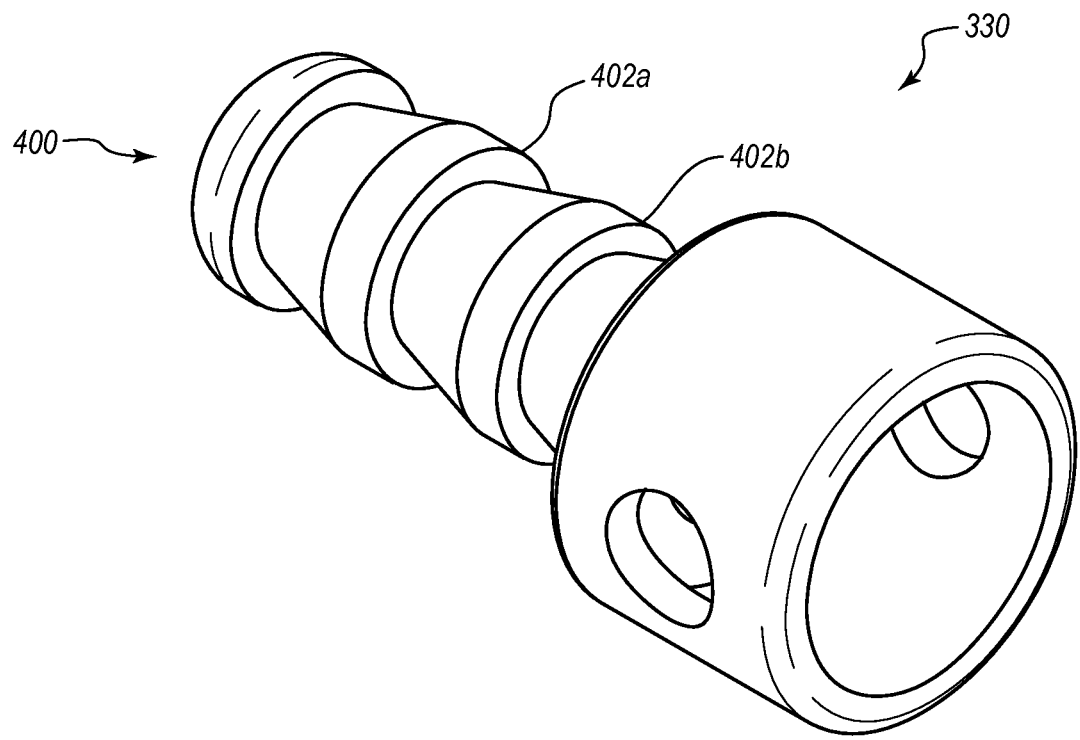
FIGS. 4A and 4B are a perspective view and a cross-sectional view, respectively, of a stepped connector of the adjustable annuloplasty ring of FIGS. 3A and 3B according to one embodiment.
Figure 4B:
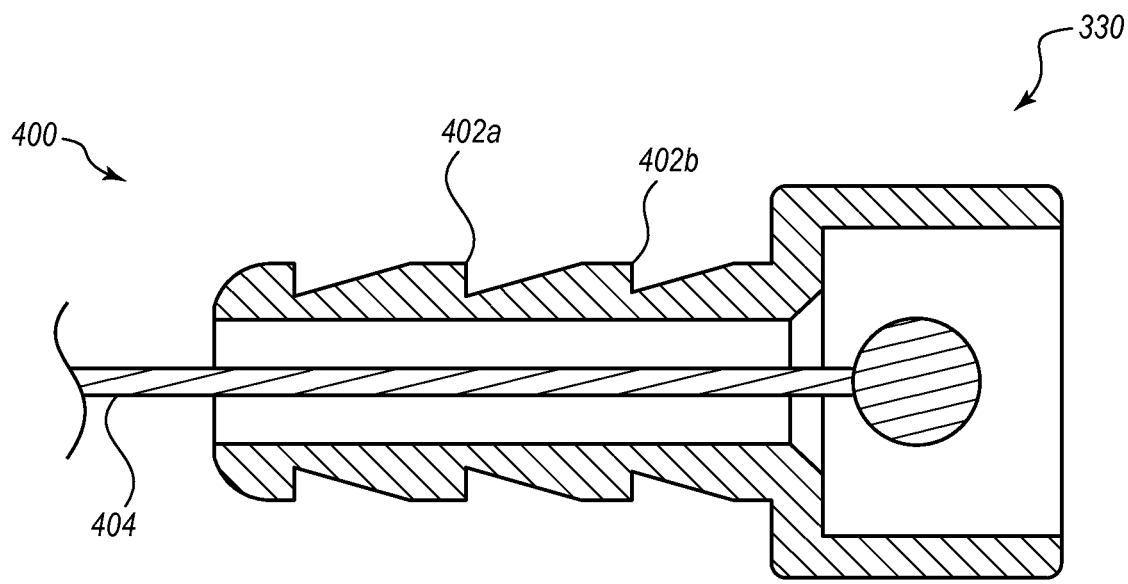

FIGS. 4A and 4B are a perspective view and a cross-sectional view, respectively, of a male component 400 of a stepped connector 330 of the adjustable annuloplasty ring 300 of FIGS. 3A and 3B according to one embodiment. A corresponding female component (not shown) may be configured to receive the male component 400 to form the stepped connector 330. The stepped connector 330 may include two engagement steps 402a, 402b (collectively 402) to allow two degrees of adjustment and/or gradual adjustment. As shown in FIG. 4B, a cable 404 or suture may couple to the male component 400 of the stepped connector 330. The cable 404 or suture may enable a force to move the male component 400 in a telescopic manner into a female component of the stepped connector 330. Contraction of the annuloplasty ring 300 until engagement of a first engagement step 402a within the female component may secure the annuloplasty ring 300 in a partial contracted state. Further contraction of the annuloplasty ring 300 to engagement of a second engagement step 402b within the female component may secure the annuloplasty ring 300 in the contracted state. In this manner, the stepped connector 330 enables two degrees of adjustment (and for gradual adjustment) of the A-P distance of the annuloplasty ring.

Example Embodiments of Anchors

Figure 5A:
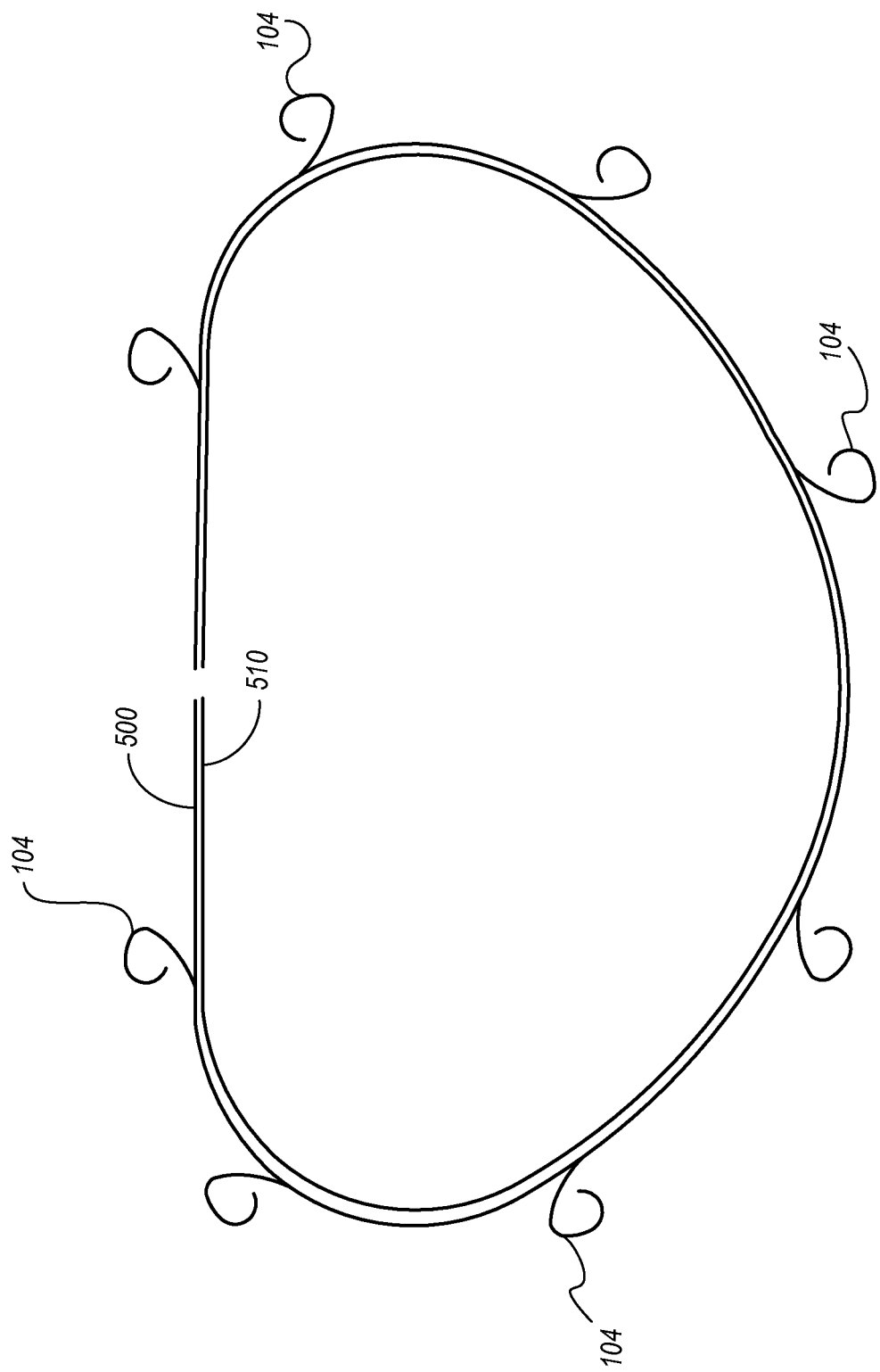
FIG. 5A is a simplified schematic diagram illustrating a side view of an internal anchor ribbon including the curved anchors shown in FIGS. 1A and 1B according to one embodiment.

FIG. 5A is a simplified schematic diagram illustrating a side view of an internal anchor ribbon 500 including the curved anchors 104 shown in FIGS. 1A and 1B according to one embodiment. In certain embodiments, deployment of the anchors 104 is accomplished using an internal anchor member, such as anchor ribbon 500, that is selectively movable within a hollow tube of the body member 101 (FIG. 1A). The curved anchors 104 may be affixed (e.g., laser welded) to the internal anchor ribbon 500 or directly cut into the internal anchor ribbon 500. Like the anchors 104, the internal anchor ribbon 500 may include a superelastic shape memory material (e.g., Nitinol). The shape memory of the anchor ribbon 500 may be heat set to the same memorized annular shape as the plurality of regions 102 of the body member 101 in the contracted state of the annular operable geometry, as shown in FIGS. 1A and 1B.

The internal anchor ribbon 500 may be slid (e.g., using wires or sutures accessible through the catheter) within the hollow body member 101 of the annuloplasty ring 100. To reduce friction between the internal anchor ribbon 500 and the body member 101, certain ring embodiments include an internal glide ribbon 510. The internal glide ribbon 510 may include a low-friction material (e.g., as a coating or covering) such as PTFE or other polymer. In addition, or in other embodiments, the internal glide ribbon 510 includes a superelastic shape memory material (e.g., Nitinol) that is heat set to the same memorized annular shape as the body member 101. Thus, certain embodiments include three D-shaped superelastic members (the outer tube of the body member 101, the internal anchor ribbon 500, and the internal glide ribbon 510), which cooperate to increase the rigidity of the annuloplasty ring 100.

Figure 5B:
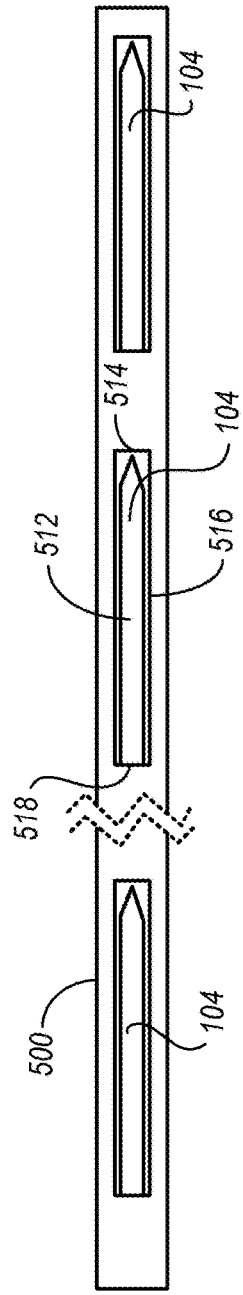
FIG. 5B is a schematic diagram illustrating a top view of the anchors cut into the internal anchor ribbon shown in FIG. 5A in the elongate insertion geometry according to one embodiment.
Figure 5C:
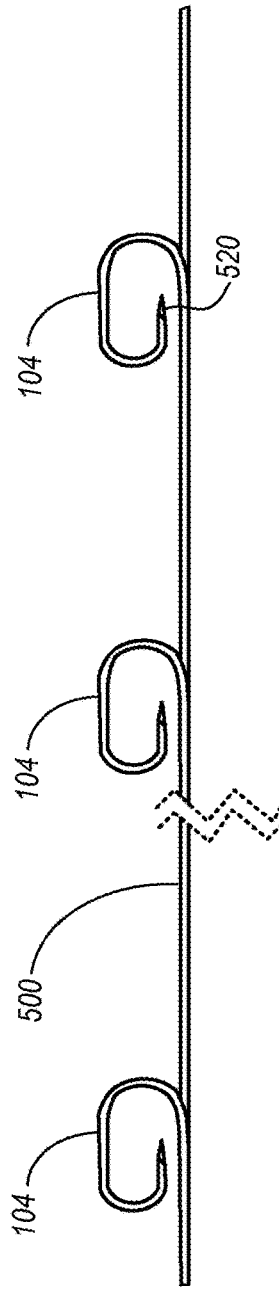
FIG. 5C is a schematic diagram illustrating a side view of the internal anchor ribbon in the elongate insertion geometry and the anchors in a curled or curved deployed configuration according to one embodiment.
Figure 5D:
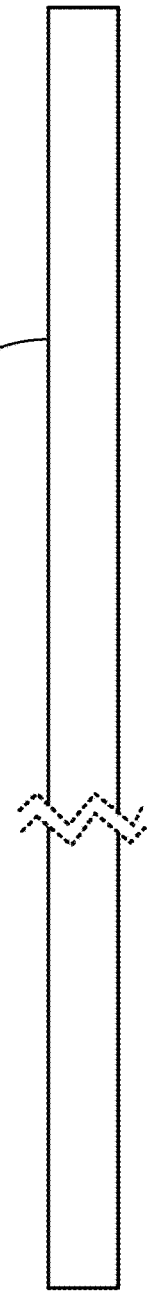
FIG. 5D is a schematic diagram illustrating a top view of an internal glide ribbon shown in FIG. 5A in an elongate insertion geometry according to one embodiment.
Figure 5E:
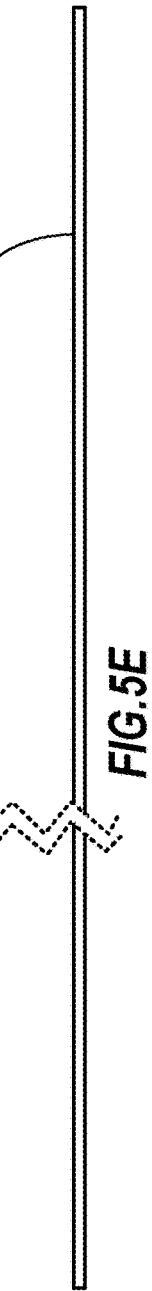
FIG. 5E is a schematic diagram illustrating a side view of the internal glide ribbon shown in FIG. 5D.

FIG. 5B is a schematic diagram illustrating a top view of the anchors 104 cut into the internal anchor ribbon 500 shown in FIG. 5A in the elongate insertion geometry according to one embodiment. In this example, a laser is used to cut the anchors 104 along a first side 512, a second side 514 (e.g., in a pointed or tip shape), and a third side 516, while leaving a fourth side 518 of the anchor 104 uncut and attached to the internal anchor ribbon 500. After cutting, the anchors 104 are heat set to the desired memorized shape for the deployed configuration. For example, FIG. 5C is a schematic diagram illustrating a side view of the internal anchor ribbon 500 in the elongate insertion geometry and the anchors 104 in a curled or curved deployed configuration according to one embodiment. The amount of curvature in the deployed configuration of the anchors 104 may depend on the particular application. In the example shown in FIG. 5C, the anchors 104 fold back on themselves such that the prong or tip 520 points parallel to or away from the internal anchor ribbon 500. FIG. 5D is a schematic diagram illustrating a top view of the internal glide ribbon 510, and FIG. 5E is a schematic diagram illustrating a side view of the internal glide ribbon 510, in the elongate insertion geometry according to one embodiment.

FIGS. 6A and 6B are simplified schematics illustrating cross-section side views of an annuloplasty ring 600 before (FIG. 6A) and after (FIG. 6B) deployment of the anchors 104 shown in FIGS. 5A-5C according to one embodiment. For illustrative purposes, the annuloplasty ring 600 in FIGS. 6A and 6B is shown in an elongate insertion geometry. Artisans will recognize from the disclosure herein, however, that the anchors 104 are generally deployed when the annuloplasty ring 600 is in the annular operable geometry.

The illustrated annuloplasty ring 600 includes an outer tube 610 (e.g., formed by the body member 101 shown in FIG. 1) including a plurality of anchor deployment windows 612. During the manufacturing of the annuloplasty ring 600, and before the annuloplasty ring 600 is loaded into the catheter, the internal anchor ribbon 500 and the internal glide ribbon 510 are inserted into the outer tube 610 in a position where the anchors 104 are prevented from exiting through the windows 612. As shown in FIG. 6A, inserting the internal anchor ribbon 500 into the outer tube 610 prevents the anchors from assuming their fully curved deployed configuration.

For deploying the anchors 104, the internal anchor ribbon 500 may include (or may be attached to) a hook or loop 614 for engaging a wire or suture 616 that may be pulled by a user through the catheter (e.g., in the direction of arrow 618 in FIG. 6A) to move the tip of each anchor 104 to a corresponding window 612. In certain embodiments, the anchors 104 and windows 612 are arranged such that the tip of each anchor 104 reaches its respective window 612 at substantially the same time as the other anchor/window pairs. As shown in FIG. 6B, once the tips of the anchors 104 reach the respective windows 612, the superelasticity of the anchors 104 propels the internal anchor ribbon 500 in the opposite direction (as indicated by arrow 620) as the anchors 104 spring out the windows 612 (as indicated by arrow 622) to resume their curved configurations. As the anchors 104 drive through the windows 612 the anchors 104 drive into surrounding tissue (e.g., the heart valve annulus). The superelasticity of the anchors 104 allows the anchors 104 to be self-propelled into the tissue adjacent or proximate to the annuloplasty ring 600.

Figure 7:
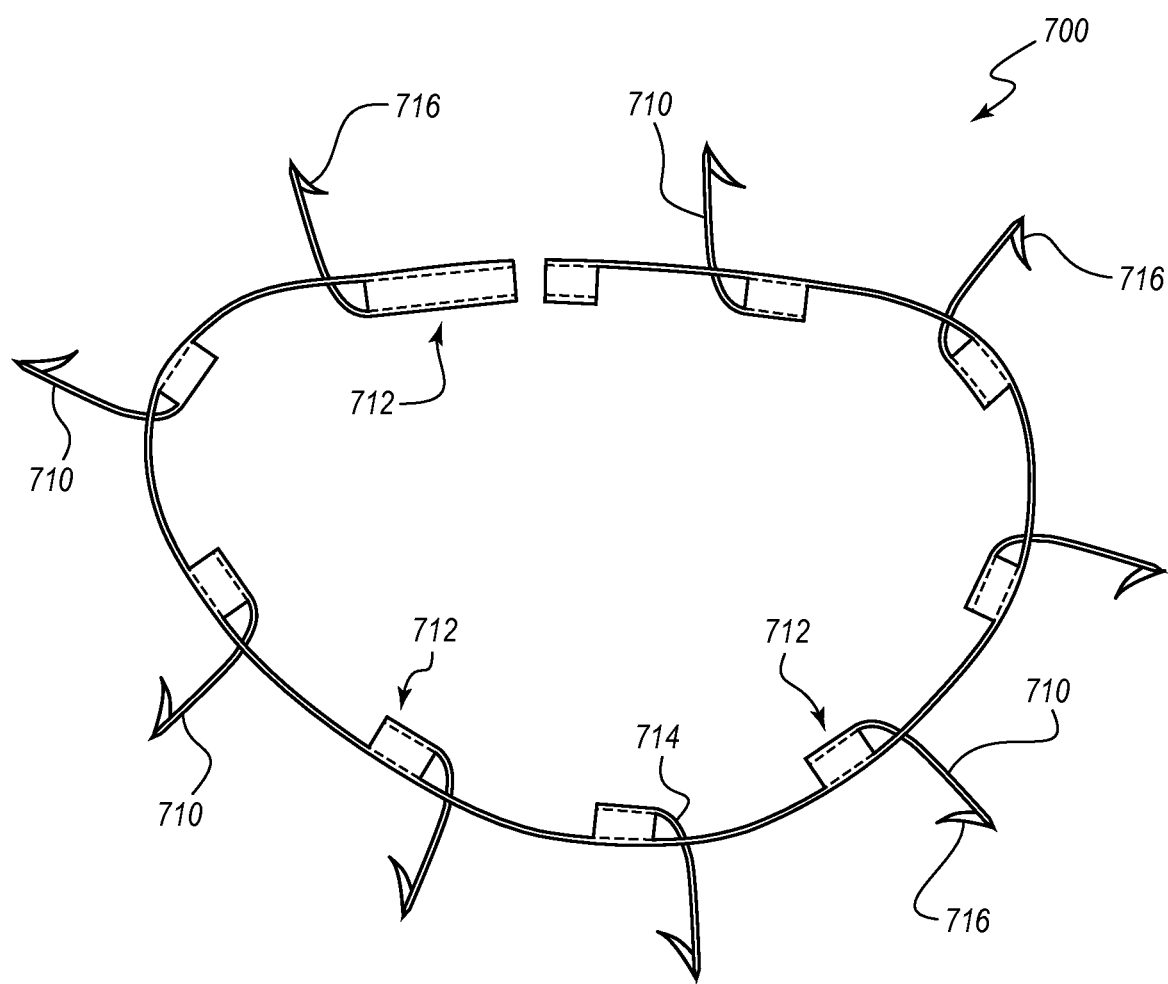
FIG. 7 is a schematic diagram illustrating a side view of an internal anchor member including linear anchors according to one embodiment.

FIG. 7 is a simplified schematic diagram illustrating a side view of an internal anchor member 700 including linear anchors 710 according to one embodiment. The linear anchors 710 may be affixed (e.g., laser welded) to the internal anchor member 700. In the embodiment shown in FIG. 7, however, the internal anchor member 700 and linear anchors 710 are cut from a single superelastic shape memory (e.g., Nitinol) hypotube. FIG. 7, for example, shows remaining tubular portions 712 after the hypotube is cut to form prongs 714 of the linear anchors 710. The remaining tubular portions 712 facilitate sliding (e.g., using wires or sutures accessible through the catheter) the internal anchor member 700 coaxially within the hollow tube of the annuloplasty ring (e.g., within the annuloplasty ring 600 shown in FIG. 6).

The internal anchor member 700 is heat set to the same memorized annular shape as the annuloplasty ring 600. The anchor prongs 714 can be heat set to protrude outward through windows cut in the annuloplasty ring 600. Barbs 716 may be laser welded to the prongs 714 to form the linear anchors 710. The linear anchors 710 are retracted/deployed by sliding the internal anchor member 700 within the annuloplasty ring 600.

Example Deployment Approaches

Figure 8A:
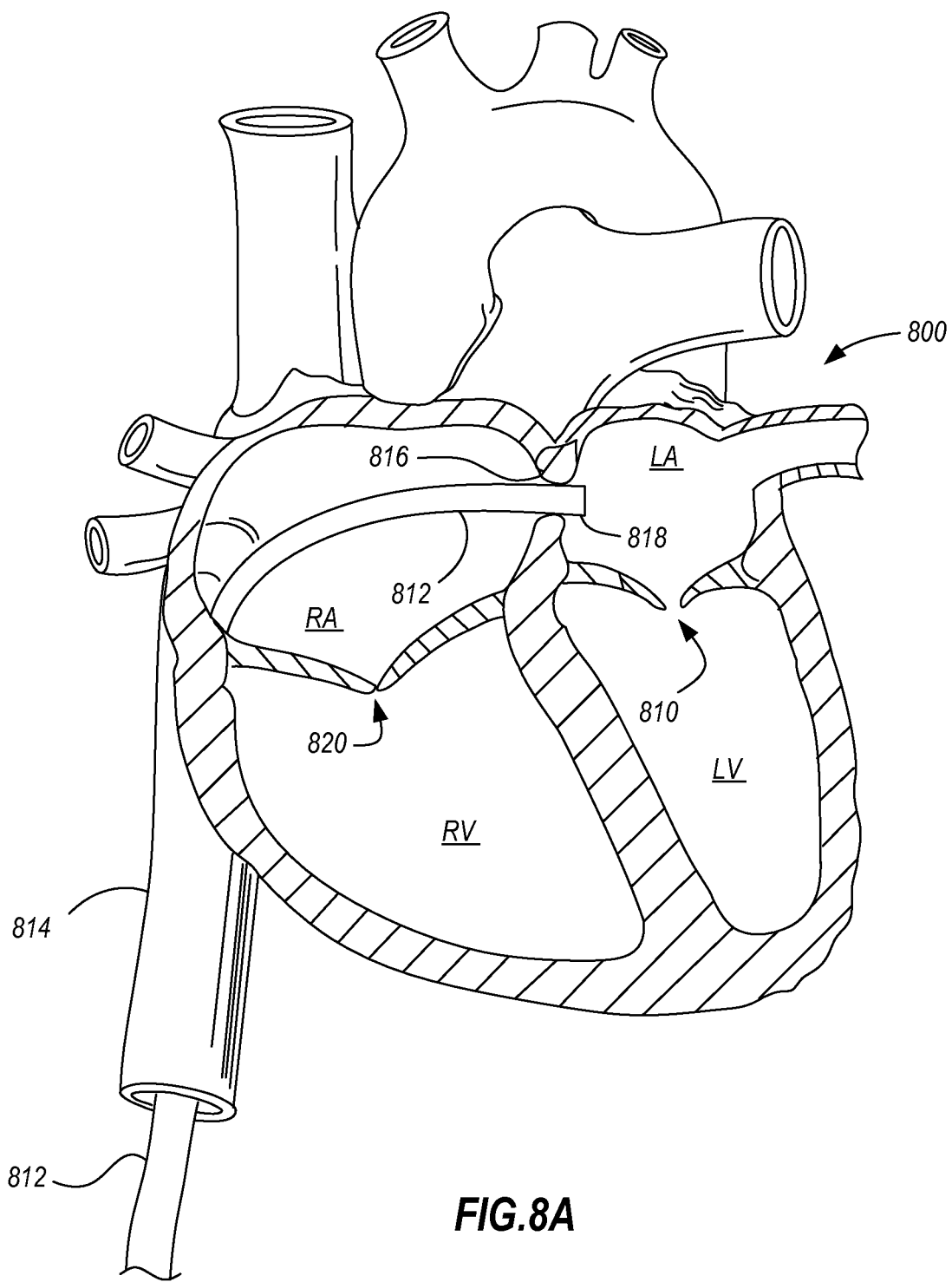
FIG. 8A is a schematic diagram illustrating a trans-septal approach for endovascular delivery of an annuloplasty ring to the mitral valve of a heart according to one embodiment.

As discussed above, the annuloplasty ring embodiments disclosed herein are configured for percutaneous transcatheter delivery and fixation to heart valves. The annuloplasty rings may be delivered through a catheter to the mitral valve, for example, using a trans-septal approach, a retrograde approach, or a trans-apical approach. For example, FIG. 8A is a schematic diagram illustrating a trans-septal approach for endovascular delivery of an annuloplasty ring (not shown) to the mitral valve 810 of a heart 800 according to one embodiment. For illustrative purposes, a partial cross-section of the heart 800 is illustrated to show the right atrium RA, right ventricle RV, left atrium LA, and left ventricle LV.

For clarity, certain features (e.g., papillary muscles and chordae tendineae) are not shown. In the trans-septal approach shown in FIG. 8A, the left atrium LA is approached by advancement of a catheter 812 through the inferior vena cava 814, into the right atrium RA, across the interatrial septum 816, and into the left atrium LA. The annuloplasty ring may then be delivered through the catheter 812 into the atrium and anchored to the annulus of the mitral valve 810.

As shown in FIG. 8A, the catheter 812 is delivered percutaneously into the heart 800. A guiding sheath (not shown) may be placed in the vasculature system of the patient and used to guide the catheter 812 and its distal end 818 to a desired deployment site. In some embodiments, a guide wire (not shown) is used to gain access through the superior or inferior vena cava 814, for example, through groin access for delivery through the inferior vena cava 814. The guiding sheath may be advanced over the guide wire and into the inferior vena cava 814 shown in FIG. 8A. The catheter 812 may be passed through the right atrium RA and toward the interatrial septum 816. Once the distal end 818 of the catheter 812 is positioned proximate to the interatrial septum 816, a needle or piercing member (not shown) is advanced through the catheter 812 and used to puncture the fossa ovalis or other portion of the interatrial septum 816. In some embodiments, the catheter 812 is dimensioned and sized to pass through the fossa ovalis without requiring a puncturing device. That is, the catheter 812 may pass through the natural anatomical structure of the fossa ovalis into the left atrium LA.

Similarly, any chamber (LV, RV, LA, RA) of the heart 800 may be approached through the inferior vena cava 814. For example, the right ventricle RV may be approached through the inferior vena cava 814, into the right atrium RA, and through the tricuspid valve 820. A variety of other endovascular approaches may also be used.

Figure 8B:
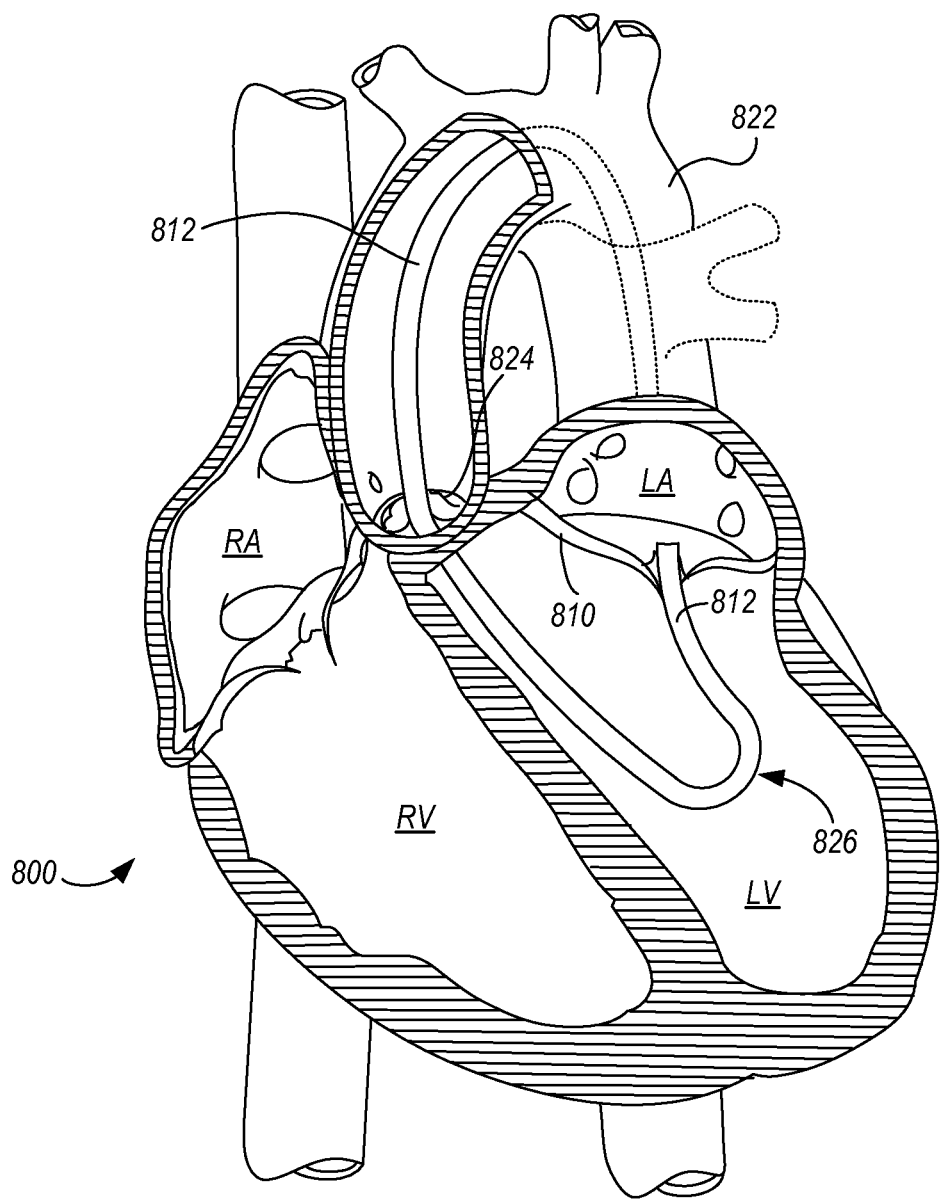
FIG. 8B is a schematic diagram illustrating an example retrograde approach of an annuloplasty ring to the mitral valve of a heart according to another embodiment.

FIG. 8B is a schematic diagram illustrating an example retrograde approach of an annuloplasty ring (not shown) to the mitral valve 810 of a heart 800 according to another embodiment. In FIG. 8B, a femoral approach is shown wherein the delivery catheter 812 is advanced through the aorta 822 and the aortic valve 824. Typically, the catheter 812 is advanced through a sheath positioned within the femoral artery (not shown). Under fluoroscopy or other methods of guidance, the distal end of the catheter 812 is guided within the left ventricle LV and turned (e.g., as shown with a "U-turn" 826) within the left ventricle LV so as to pass through the leaflets of the mitral valve 810 and into the left atrium LA. After verification of the appropriate positioning of the catheter 812, a guide wire (not shown) may be inserted through the catheter 812 into the left atrium LA, which may then be used to guide one or more other catheters into the left atrium LA for delivering and anchoring the annuloplasty ring to the annulus of the mitral valve 810.

Figure 8C:
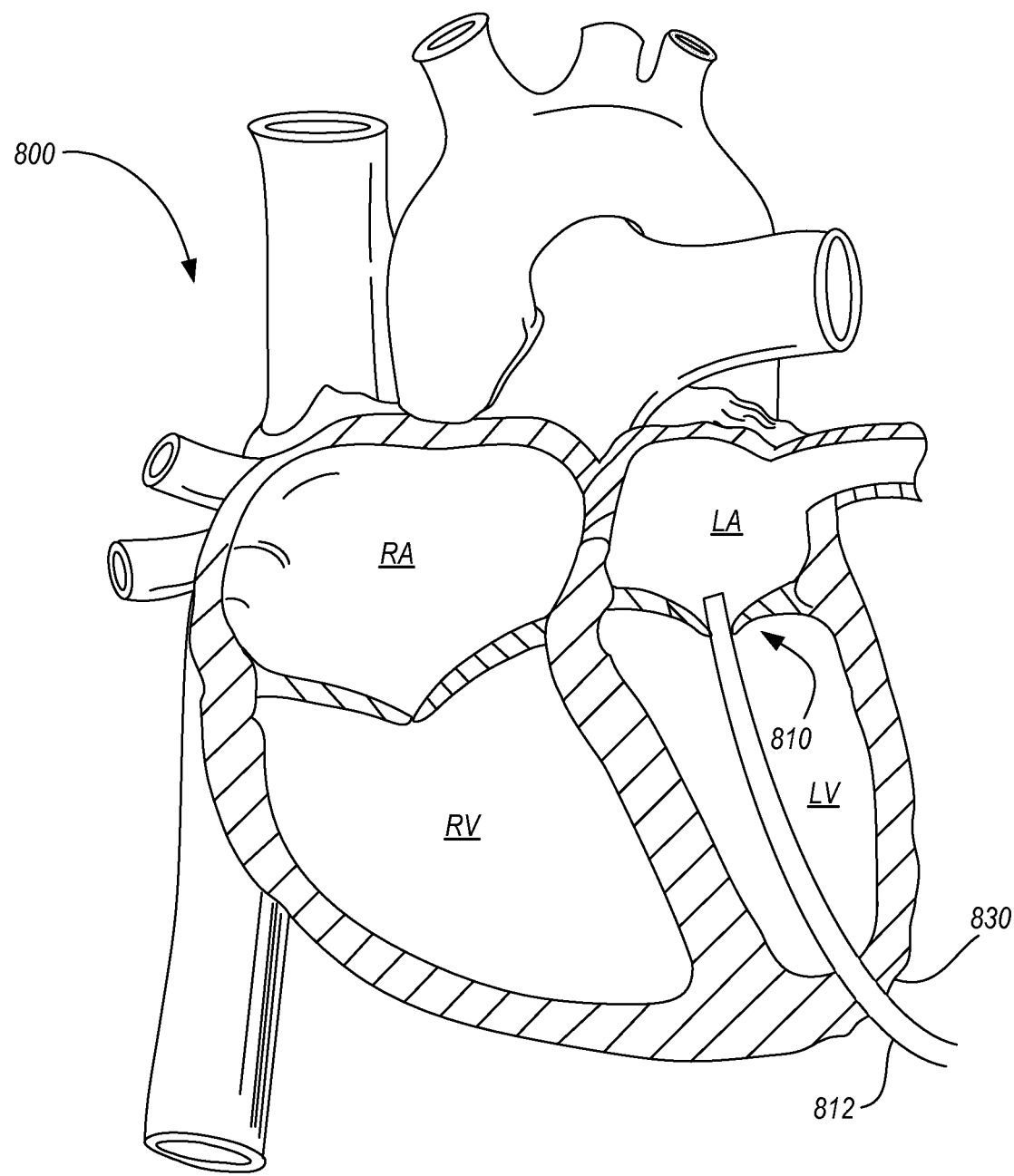
FIG. 8C is a schematic diagram illustrating an example trans-apical approach of an annuloplasty ring to the mitral valve of a heart according to another embodiment.

FIG. 8C is a schematic diagram illustrating an example trans-apical approach of an annuloplasty ring (not shown) to the mitral valve 810 of a heart 800 according to another embodiment. In this example, the catheter 812 is shown passing through the apex 830 of the heart 800, through the left ventricle LV, through the leaflets of the mitral valve 810, and into the left atrium. The annuloplasty ring may be delivered through the catheter 812 into the left atrium LA and anchored to the annulus of the mitral valve 810. In one embodiment, a needle or trocar may be used to puncture through the apex 830 to create a small opening through which a guide wire (not shown) can be inserted through the left ventricle LV into the left atrium LA. Then, the guide wire may be used to guide successively larger and stiffer catheters so as to gradually increase the size of the opening in the apex 830 of the heart 800.

Figure 9A:
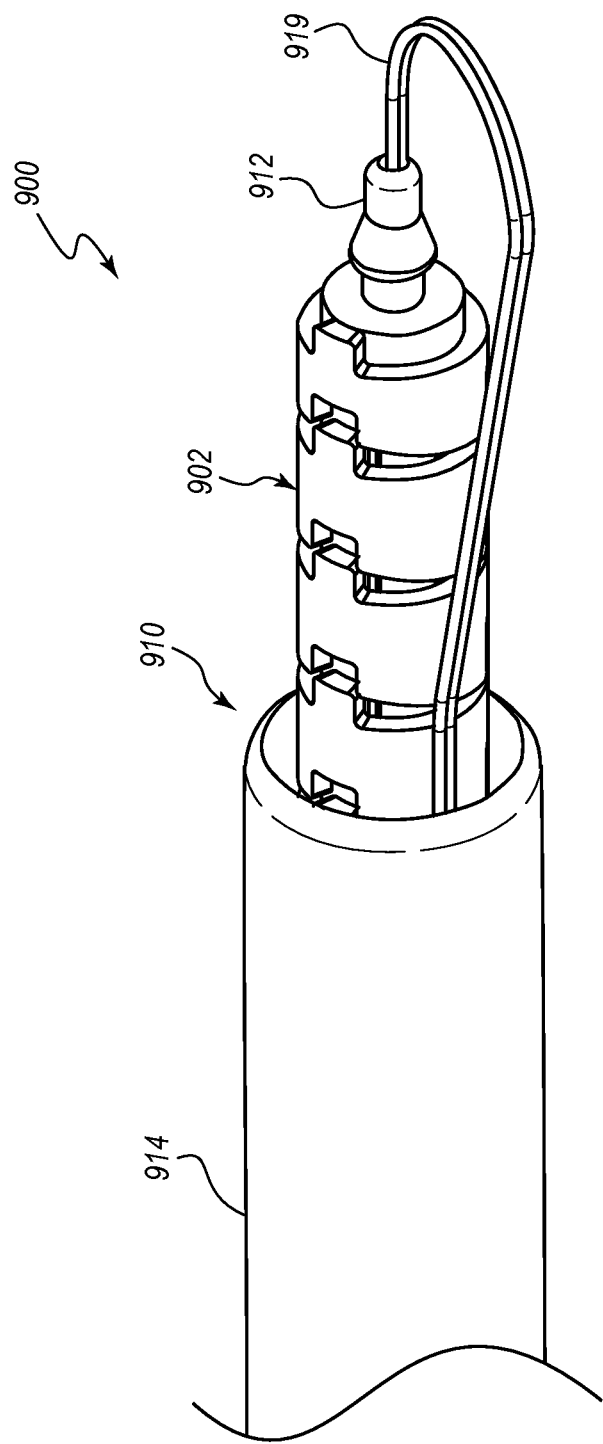
FIGS. 9A, 9B, 9C, and 9D are schematic diagrams illustrating transcatheter delivery of an annuloplasty ring from a delivery system according to certain embodiments.

FIGS. 9A, 9B, 9C, and 9D are schematic diagrams illustrating transcatheter delivery of an annuloplasty ring 902 from a delivery system 900 according to certain embodiments. FIG. 9A illustrates a perspective view of a distal end 910 of the delivery system 900. FIG. 9A is a perspective view of the annuloplasty ring 902 in the elongate insertion geometry and partially deployed from the distal end 910 of a delivery catheter 914 in a first deployment stage. In the first stage, the annuloplasty ring 902 may be still substantially in the elongate insertion geometry. As shown in FIG. 9A, a first suture 919 for snapping together the ends of the annuloplasty ring 902 passes through a male snap 912 of a ring closure lock 950 (shown in FIG. 9C).

Figure 9B:
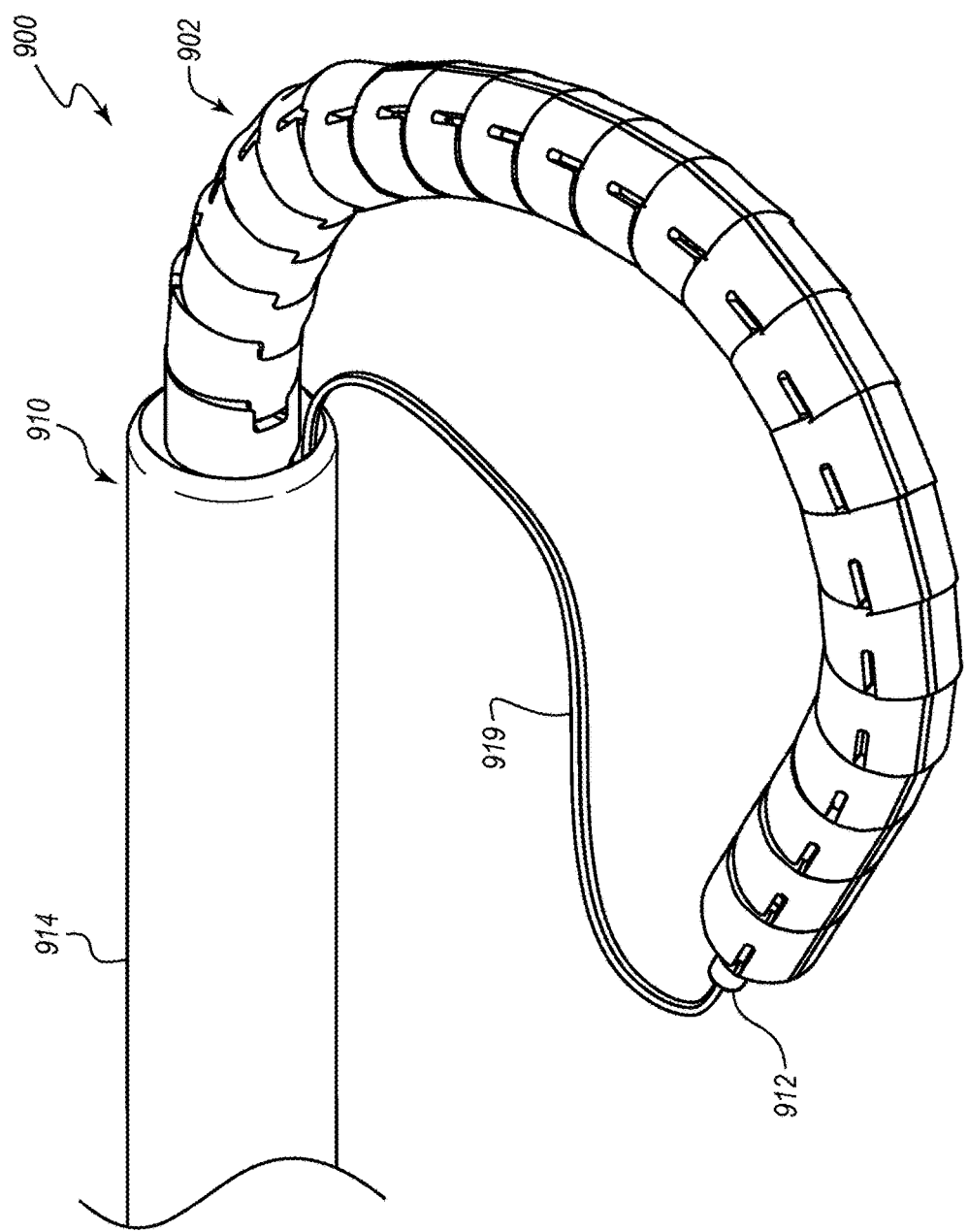

FIG. 9B is a perspective view of the annuloplasty ring 902 in a second stage of partial deployment from the delivery catheter 914. In the second stage, the portion of the annuloplasty ring 902 that has exited the delivery catheter 914 has begun to transition (due to the shape memory materials used in the annuloplasty ring 902) from the elongate insertion geometry to the annular operable geometry.

Figure 9C:
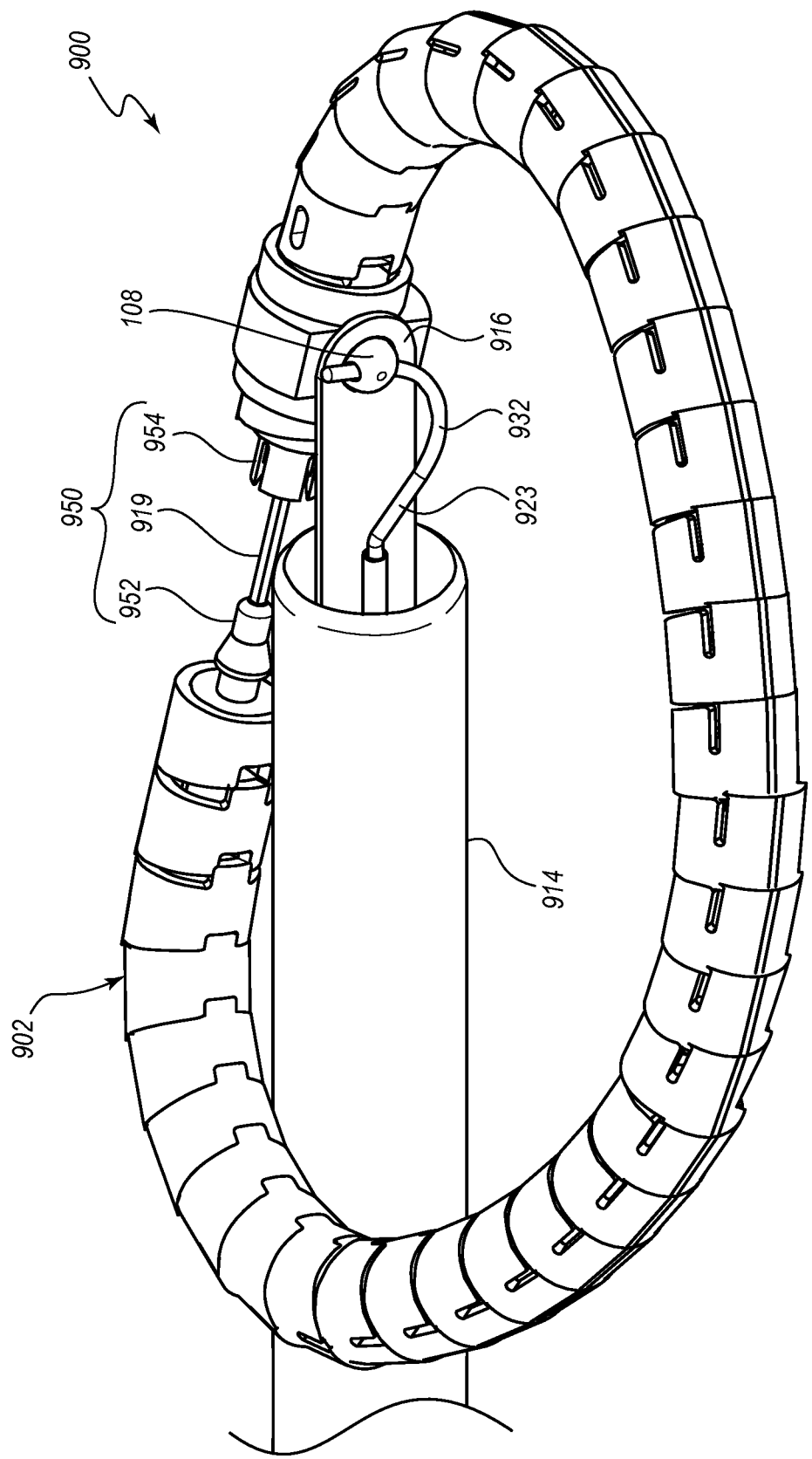

FIG. 9C is a perspective view of the annuloplasty ring 902 in a third stage of deployment in which a ring shuttle 916 of the delivery system 900 has substantially pushed the annuloplasty ring 902 out of the delivery catheter 914, but the plane of the annuloplasty ring 902 is still aligned with (e.g., approximately parallel to) the longitudinal axis of the delivery catheter 914. In FIG. 9C, the annuloplasty ring 902 may be in a configuration, for example, immediately before a ring deployment wire 923 cooperates with the pivot 108 to rotate the annuloplasty ring 902 (see FIG. 9D). In the configuration shown in FIG. 9C, the distal end of the ring deployment wire 923 includes a bend or hook 932 as it passes through a hole in the pivot 108. The ring deployment wire 923 includes a superelastic shape memory material (e.g., Nitinol), and bending the distal end of the ring deployment wire 923 into the hook 932 shape spring loads the annuloplasty ring 902 within the outer jacket delivery catheter 914 such that the annuloplasty ring 902 automatically rotates about the pivot 108 upon exiting the outer jacket delivery catheter 914. At this third stage of deployment, the hook 932 shape formed in the superelastic ring deployment wire 923 is ready to unload (return to a heat-set memorized straight configuration) as soon as the delivery catheter 914 no longer prevents it from doing so. The suture 919 may be utilized to draw together the male components 952 and female components 954 of a ring closure lock 950.

Figure 9D:
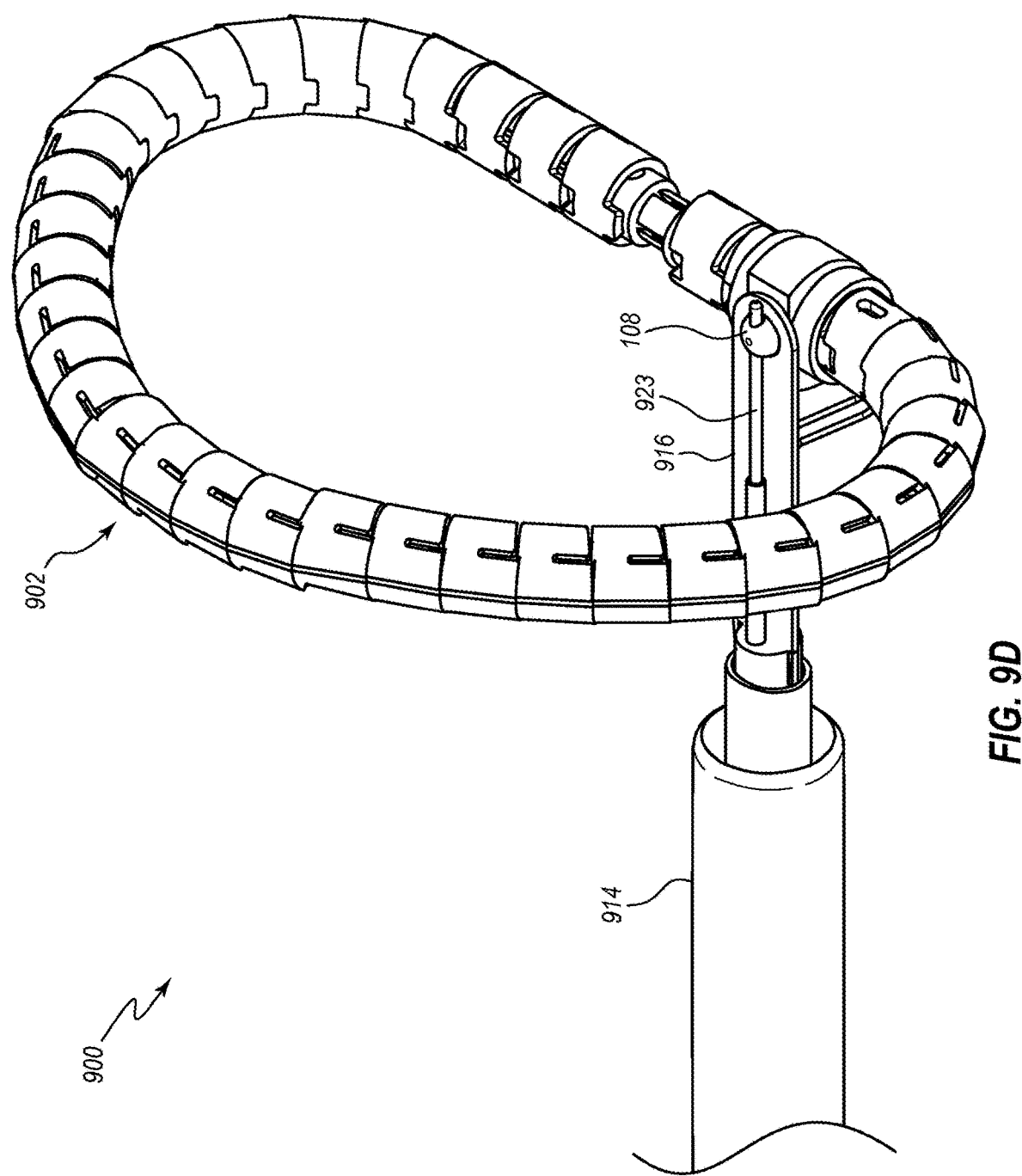

FIG. 9D is a perspective view of the annuloplasty ring 902 in a fourth stage of deployment in which the plane of the annuloplasty ring 902 (in its annular operable geometry) has been changed to be perpendicular to the longitudinal axis of the delivery catheter 914. As shown in FIG. 9D, the superelastic ring deployment wire 923 has returned to its heat set (memorized) straight configuration. At this fourth stage of deployment, the plane of the annuloplasty ring 902 is configured to be parallel to the plane of the heart valve annulus. In situ within the heart, a longitudinal axis of the delivery catheter 914 is oriented parallel to the direction of blood through the valve and approximately perpendicular to the plane of the heart valve. The annuloplasty ring 902, when oriented such that the plane of the annuloplasty ring 902 is transverse to (and perpendicular or approximately perpendicular to) the longitudinal axis of the delivery catheter 914, is oriented such that the plane of the annuloplasty ring 902 is parallel or approximately parallel to the plane of the heart valve.

In further stages of deployment, the annuloplasty ring 902 may be expanded and/or pressed against the heart valve annulus before deploying the anchors (such as the curved anchors 104 shown in FIGS. 1A and 1B). As discussed above, certain anchor embodiments propel themselves into the tissue of the heart valve annulus upon being deployed. In other embodiments, the anchors (such as the linear anchors 710 shown in FIG. 7) may be deployed before pressing the annuloplasty ring 902 against the annulus. After the annuloplasty ring 902 is anchored to the heart valve annulus and transitioned to the contracted state, the ring deployment wire 923 may be pulled from the hole in the pivot 108 to release the annuloplasty ring 902 from the ring shuttle 916. Any remaining sutures, such as the first suture 919, may also be cut and/or pulled from the annuloplasty ring 902 before the delivery catheter 914 is removed from the heart.

Example Expansion Tool Embodiments

Figure 10:
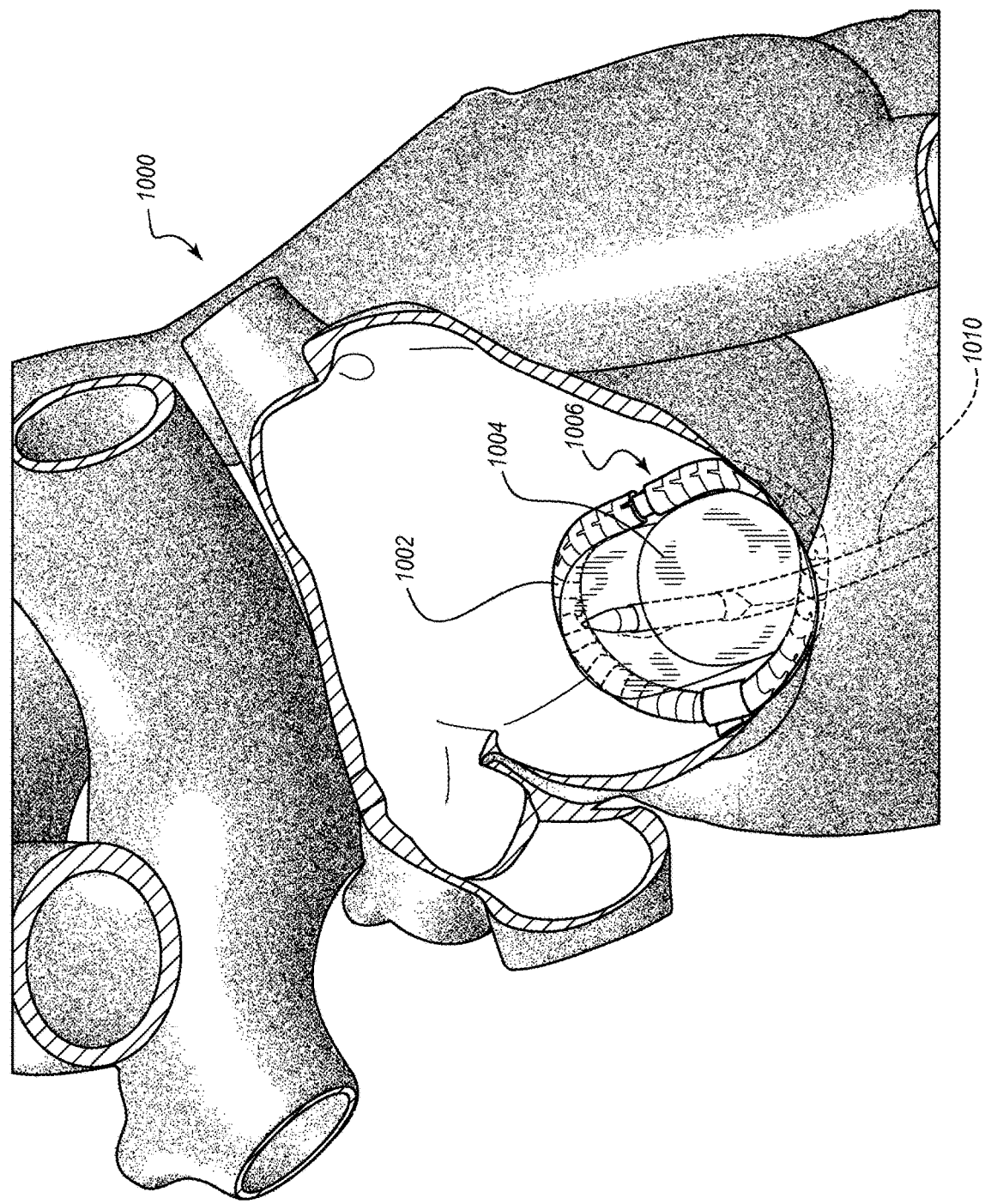
FIG. 10 is a schematic diagram illustrating a perspective, partial cross-sectional view of a heart during the expansion of an adjustable annuloplasty ring using a balloon expansion tool, preparatory to affixation to the annulus of the mitral valve according to one embodiment.

FIG. 10 is a schematic diagram illustrating a perspective, partial cross-sectional view of a heart 1000 during the expansion of an adjustable annuloplasty ring 1002 using a balloon tool 1004 as an expansion tool 1004, preparatory to affixation to the annulus of the mitral valve 1006 according to one embodiment. As shown, a delivery catheter 1010 extends from the left ventricle into the left atrium through the leaflets of the mitral valve 1006. Thus, this illustrated embodiment may correspond to, for example, a trans-apical approach or a retrograde approach, as discussed above. Artisans will recognize from the disclosure herein, however, that similar principles as those illustrated may be used for trans-septal approaches.

In FIG. 10, an expansion tool 1004 is being used to expand the annuloplasty ring 1002. The annuloplasty ring 1002 is positioned on or next to the annulus of the mitral valve 1006. The expansion tool 1004 is disposed within the annuloplasty ring 1002 (and within the mitral valve 1006) to expand the annuloplasty ring 1002 to transition it from a contracted state to an expanded state. The expansion tool 1004 of the illustrated embodiment of FIG. 10 is a balloon expansion tool 1004. The balloon expansion tool 1004 is inflated to expand the annuloplasty ring 1002 to an expanded state. The balloon expansion tool 1004 shown in FIG. 10 includes two sections and may be considered a "multi-chamber" balloon with two chambers. In other embodiments, a balloon expansion tool 1004 with a single chamber or a balloon with more than two chambers may be used.

In the embodiment shown in FIG. 10, the inflated balloon expansion tool 1004 may reduce or prevent the flow of blood through the mitral valve during at least part of the implantation procedure. In such embodiments, inflation of the balloon expansion tool 1004 may last 20 seconds or less to prevent adverse consequences of occluding the mitral valve 1006. In other embodiments, such as the embodiment of an expansion tool shown in FIGS. 11, 12A-12B, 13A-13B, and 14A-14B, blood is allowed to flow through the mitral valve 1006 during the entire procedure.

Figure 11:
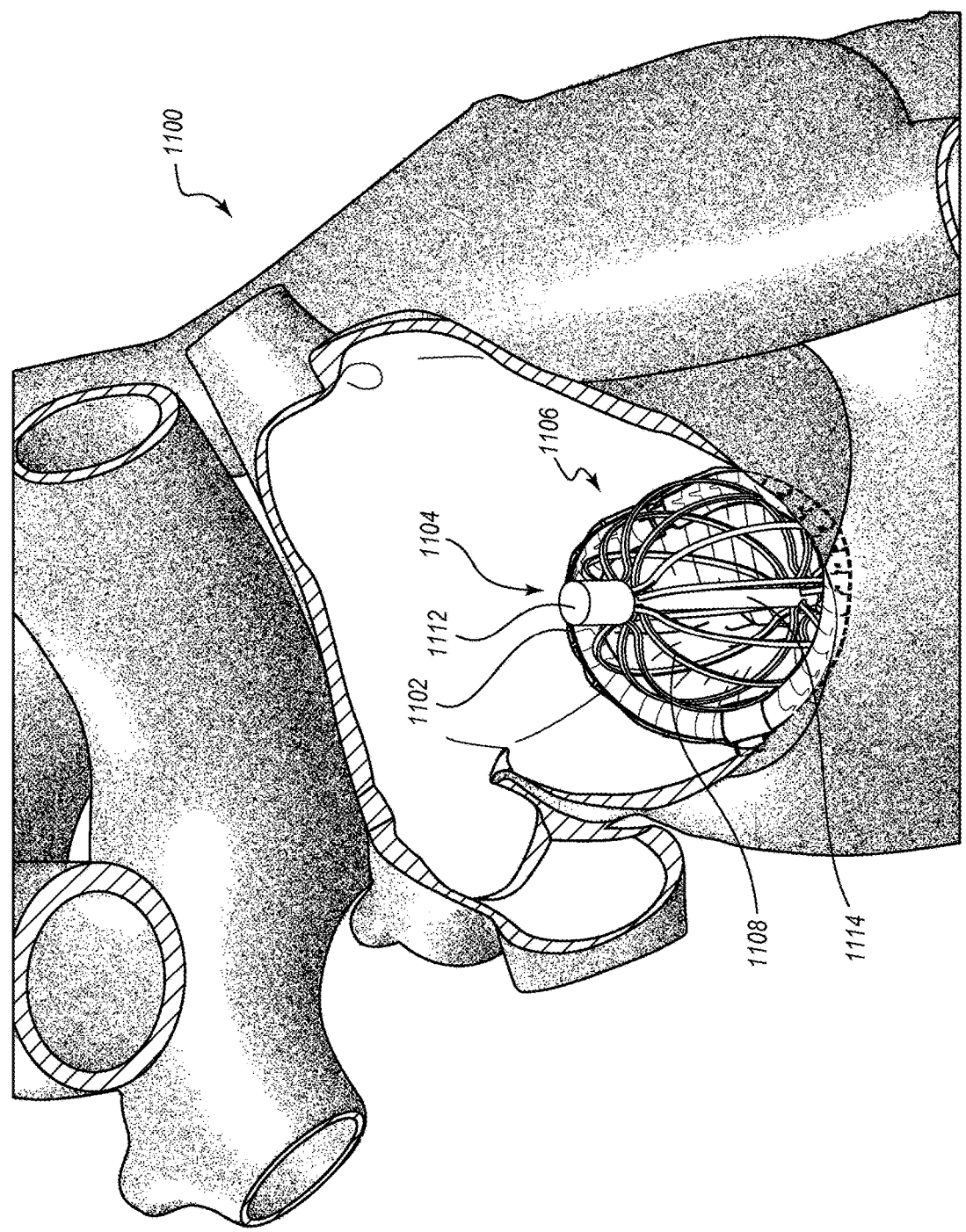
FIG. 11 is a schematic diagram illustrating a perspective, partial cross-sectional view of the heart during the expansion of an adjustable annuloplasty ring using a cage or basket expansion tool, preparatory to affixation to the annulus of the mitral valve according to another embodiment.

FIG. 11 is a schematic diagram illustrating a perspective, partial cross-sectional view of a heart 1100 during the expansion of an adjustable annuloplasty ring 1102 using a cage or basket tool 1104 as an expansion tool 1104, preparatory to affixation to the annulus of the mitral valve 1106 according to another embodiment.

The basket expansion tool 1104 may include a plurality of flexible members 1108 that lay flat against a central rod 1114 during insertion of the basket expansion tool 1104 through the delivery catheter (see FIG. 10) and may be forced into an expanded configuration (shown in FIG. 11) when the central rod 1114 is pushed into an end cap 1112. In another embodiment, each of the plurality of flexible members 1108 may comprise a superelastic material so as to spring from a delivery catheter into the expanded configuration shown in FIG. 11.

Figure 12A:
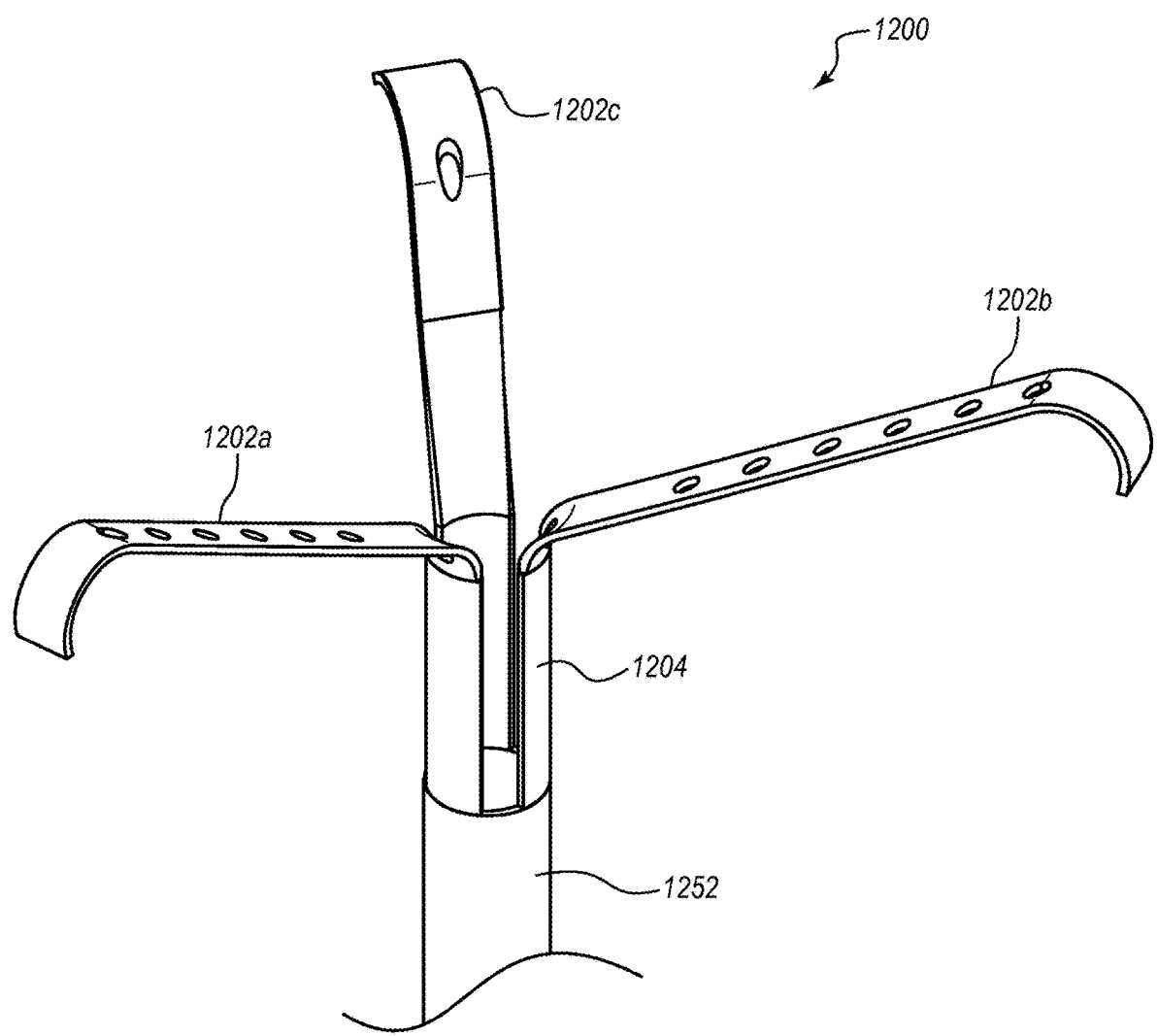
FIGS. 12A and 12B are perspective views of an intimate contact tool of a percutaneous annuloplasty system according to one embodiment.
Figure 12B:
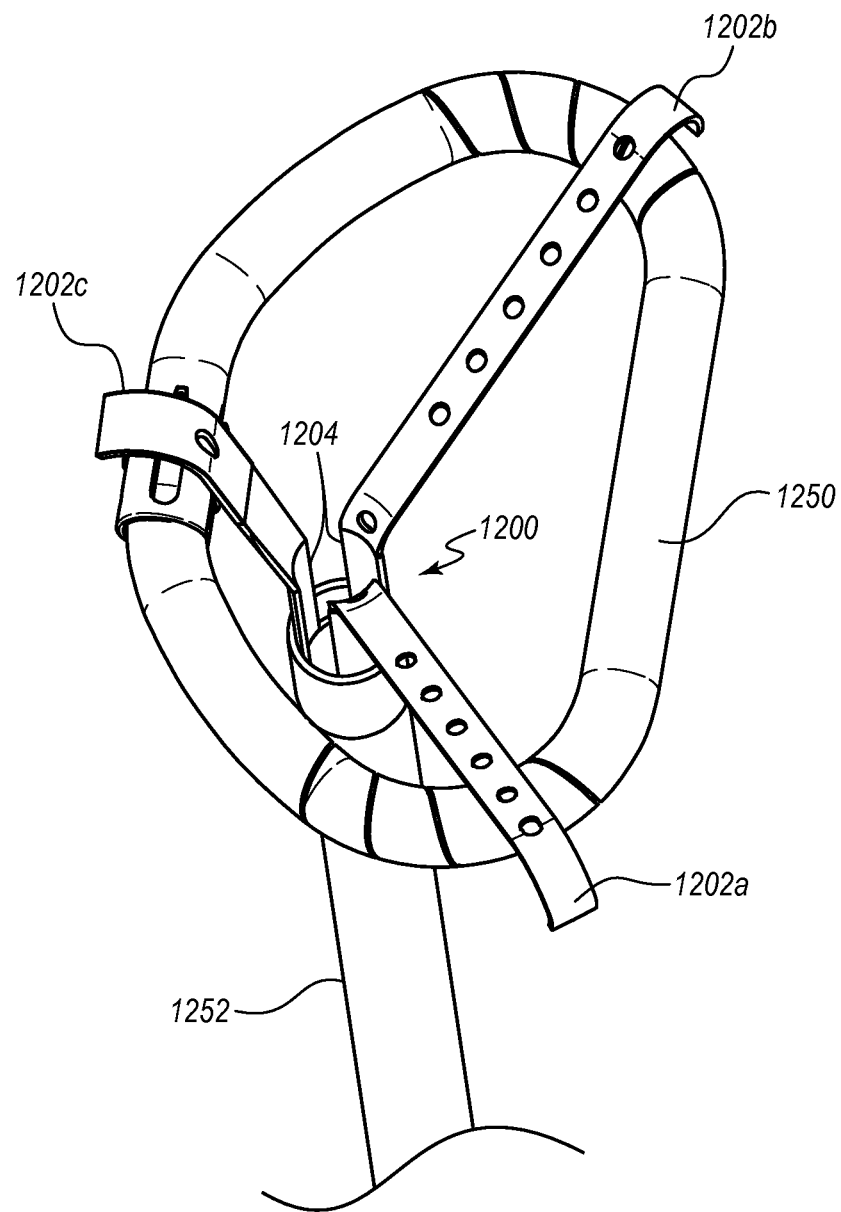

FIGS. 12A and 12B are schematic diagrams illustrating perspective views of an intimate contact tool 1200 that may be used as an expansion tool 1200 of a percutaneous annuloplasty system according to one embodiment. FIG. 12A depicts a perspective view of the intimate contact tool 1200 separated from other components of the percutaneous annuloplasty system. FIG. 12B depicts the intimate contact tool 1200 disposed through a delivery catheter 1252 and engaging an annuloplasty ring 1250.

In order to achieve good intimate contact between an annuloplasty ring 1250 (shown in FIG. 12B) and the tissue of the target heart valve (e.g., the annulus of the heart valve), the intimate contact tool 1200 may be used to position, orient, and otherwise manipulate the annuloplasty ring 1250 in the annular operable geometry, prior to affixation to tissue of the valve. The intimate contact tool 1200 may be a metallic rib structure having a plurality of arms 1202a, 1202b, 1202c (collectively 1202) or prongs configured to extend outward at an angle from a central column 1204. The rib structure, and specifically the arms 1202 and central column 1204, may be laser cut from a shape memory material, such as Nitinol. The intimate contact tool 1200 may be cut from a hollow tube to give the central column 1204 a hollow cylindrical shape. The arms 1202 may then be heat set to extend at an angle from the central column 1204.

The illustrated intimate contact tool 1200 of FIGS. 12A and 12B may include three arms 1202 arranged, for example, in the shape of a tripod. The plurality of arms 1202 of the intimate contact tool 1200 may be loaded into a delivery catheter 1252 together with the annuloplasty ring 1250 (e.g., configured in the elongate insertion geometry). As the arms 1202 emerge from a distal end of the delivery catheter 1252 they may automatically expand outward. The intimate contact tool 1200, and specifically the plurality of arms 1202, may be configured to align with and engage the annuloplasty ring 1200 as shown in FIG. 12B. When aligned and engaged with the annuloplasty ring 1250, the intimate contact tool 1200 can be used to push/pull the annuloplasty ring 1250 toward the tissue of an annulus of a heart valve.

The illustrated intimate contact tool of FIGS. 12A and 12B may be configured to engage a top surface of the annuloplasty ring 1250, through the annuloplasty ring 1250, to pull the annuloplasty ring 1250 downward. For example, the plurality of arms 1202 may include a curved, angled, or hooked portion at a distal end to facilitate engagement with the annuloplasty ring 1250. The intimate contact tool 1200 can be used to pull the annuloplasty ring 1250 toward the heart valve to facilitate intimate contact of the annuloplasty ring 1250 with the annulus. Intimate contact, or close abutment, of the annuloplasty ring 1250 with the annulus of the valve can enhance an anchor deployment process to fasten the annuloplasty ring 1250 to the annulus.

The intimate contact tool 1200, and specifically the arms 1202, may also be configured to function as an expansion tool to engage the annuloplasty ring 1250 and effectuate and/or facilitate transition of the annuloplasty ring 1250 from a contracted state to an expanded state. For example, a superelastic property and memorized shape of the plurality of arms 1202 may effectuate expansion of the annuloplasty ring 1250. The superelastic arms 1202 may engage an inner surface of the annuloplasty ring 1250 and exert outward force to expand the annuloplasty ring 1250. In other embodiments, a suture or other elongate member may enable percutaneous manipulation of one or more of the plurality of arms to effectuate expansion of the annuloplasty ring 1250.

Figure 13A:
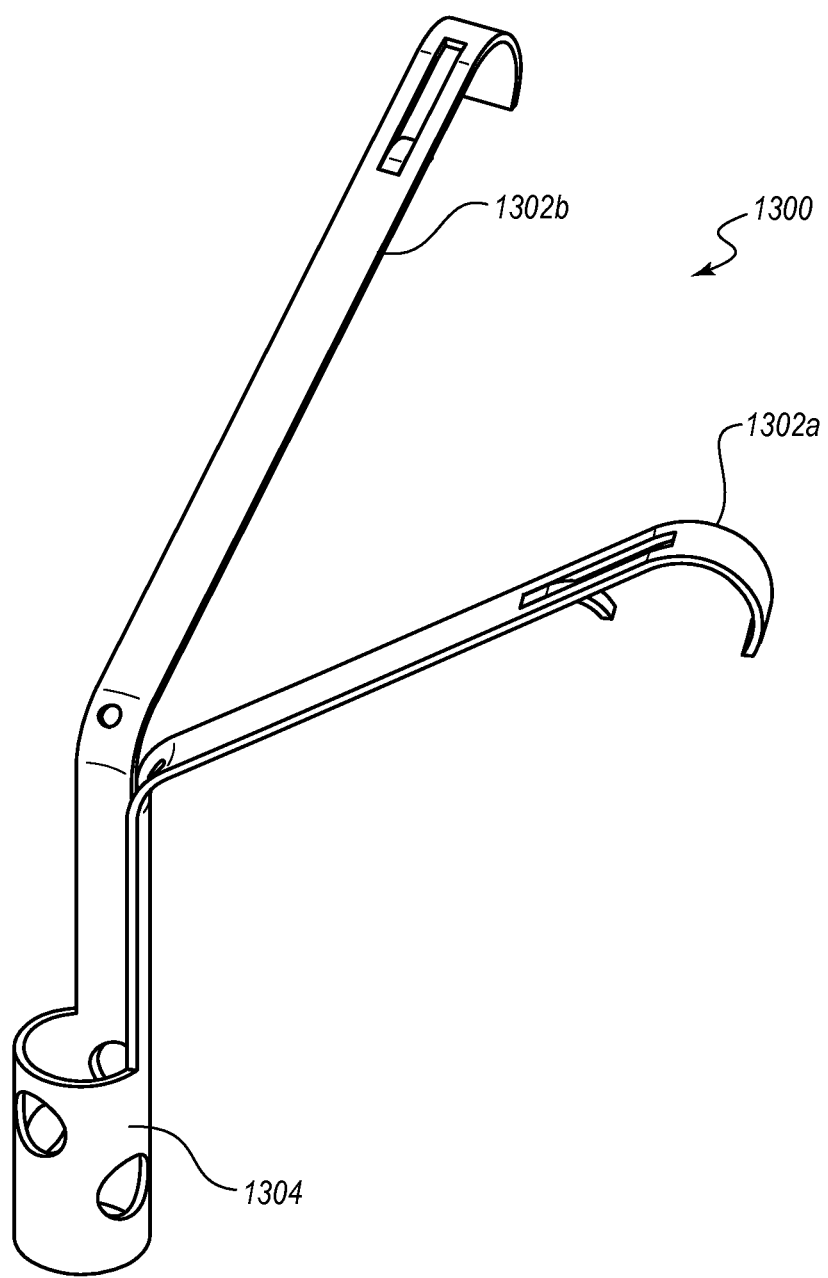
FIGS. 13A and 13B are perspective views of an intimate contact tool of a percutaneous annuloplasty system according to another embodiment.
Figure 13B:
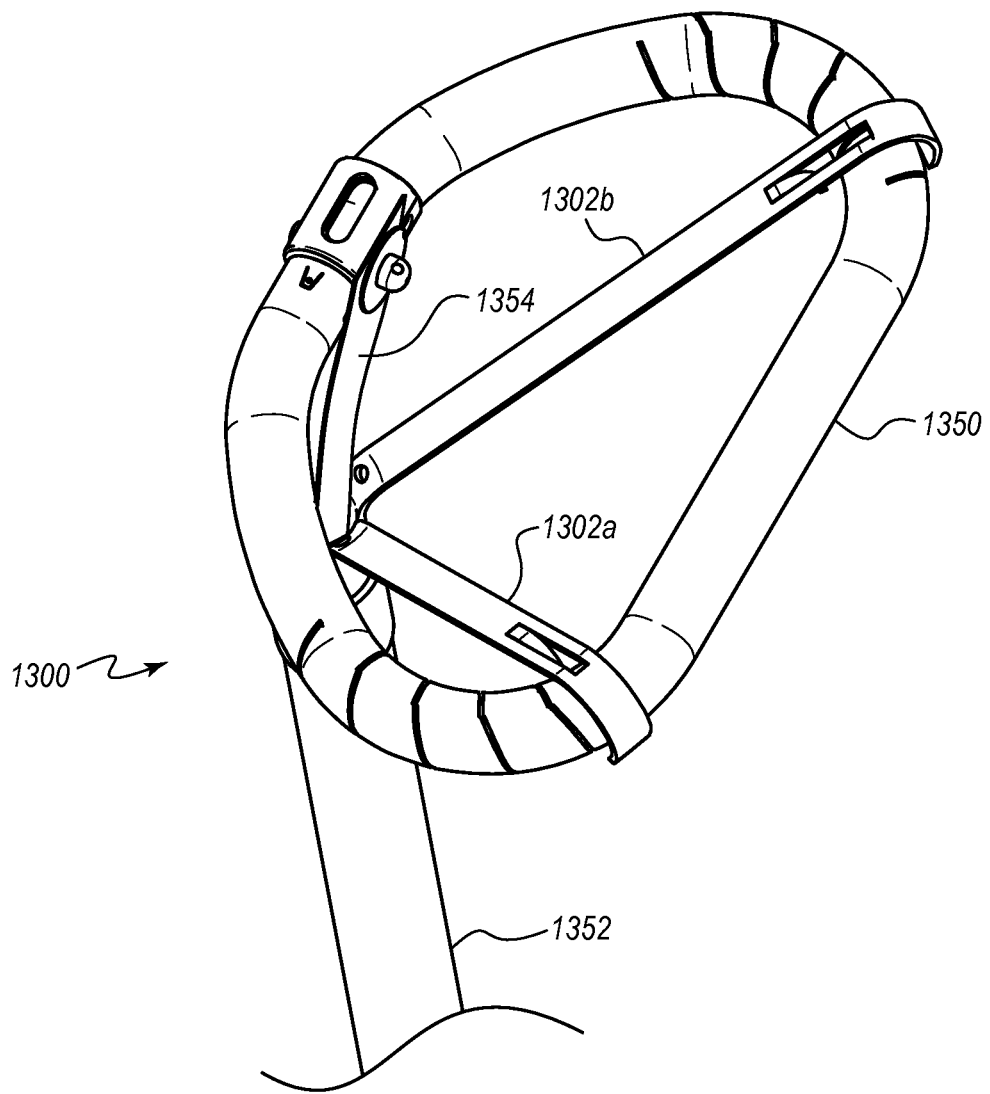

FIGS. 13A and 13B are schematic diagrams illustrating perspective views of an intimate contact tool 1300 to be used as an expansion tool of a percutaneous annuloplasty system according to another embodiment. The illustrated intimate contact tool 1300 includes only two arms 1302a, 1302b (collectively 1302) or prongs. FIG. 13A depicts a perspective view of the intimate contact tool 1300 separated from other components of the percutaneous annuloplasty system. FIG. 13B depicts the intimate contact tool 1300 disposed through a delivery catheter 1352 and engaging an annuloplasty ring 1350. The intimate contact tool 1300 may be used to position, orient, and otherwise manipulate the annuloplasty ring 1350 to achieve intimate contact in abutment with tissue of the annulus of a target heart valve.

The arms 1302 of the intimate contact tool 1300 are configured to extend outward at an angle from a central column 1304, thereby forming a rib structure. The rib structure, and specifically the arms 1302 and central column 1304, may be laser cut from a shape memory material, such as Nitinol. The intimate contact tool 1300 may be cut from a hollow tube to give the central column 1304 a hollow cylindrical shape. The arms 1302 may then be heat set to extend at an angle from the central column 1304.

The illustrated intimate contact tool 1300 of FIGS. 13A and 13B includes two arms 1302a, 1302b arranged, for example, in the shape of a bipod. The two arms 1302a, 1302b in cooperation with a ring shuttle 1354 of a delivery system of the percutaneous annuloplasty system form a tripod structure engaging the annuloplasty ring 1350 at three points. The plurality of arms 1302 may be loaded into a delivery catheter 1352 together with the annuloplasty ring 1350 (e.g., configured in the elongate insertion geometry). As the arms 1302 emerge from a distal end of the delivery catheter 1352 they may automatically expand outward and may be configured to align with and engage the annuloplasty ring 1350 as shown in FIG. 13B. When aligned and engaged with the annuloplasty ring 1350, the intimate contact tool 1300 can be used to push/pull the annuloplasty ring 1350 toward the tissue of the annulus of a heart valve.

The illustrated intimate contact tool of FIGS. 13A and 13B may be configured to engage a top surface of the annuloplasty ring 1350 to pull the annuloplasty ring 1350. For example, the plurality of arms 1302 may include a curved, angled, or hooked portion at a distal end to facilitate engagement with the annuloplasty ring 1350. The intimate contact tool 1300 can be used to pull the annuloplasty ring 1350 toward the heart valve to facilitate intimate contact of the annuloplasty ring 1350 with the annulus to enhance an anchor deployment process to fasten the annuloplasty ring 1350 to the annulus.

The intimate contact tool 1300, and specifically the arms 1302, may also be configured to function as an expansion tool to engage the annuloplasty ring 1350 and effectuate and/or facilitate transition of the annuloplasty ring 1350 from a contracted state to an expanded state. For example, a superelastic property and memorized shape of the plurality of arms 1302 may enable the arms 1302 to engage an inner surface of the annuloplasty ring 1350 and exert outward force to expand the annuloplasty ring 1350. In other embodiments, a suture or other elongate member may enable percutaneous manipulation of one or more of the plurality of arms 1302 to effectuate expansion of the annuloplasty ring 1350.

Figure 14A:
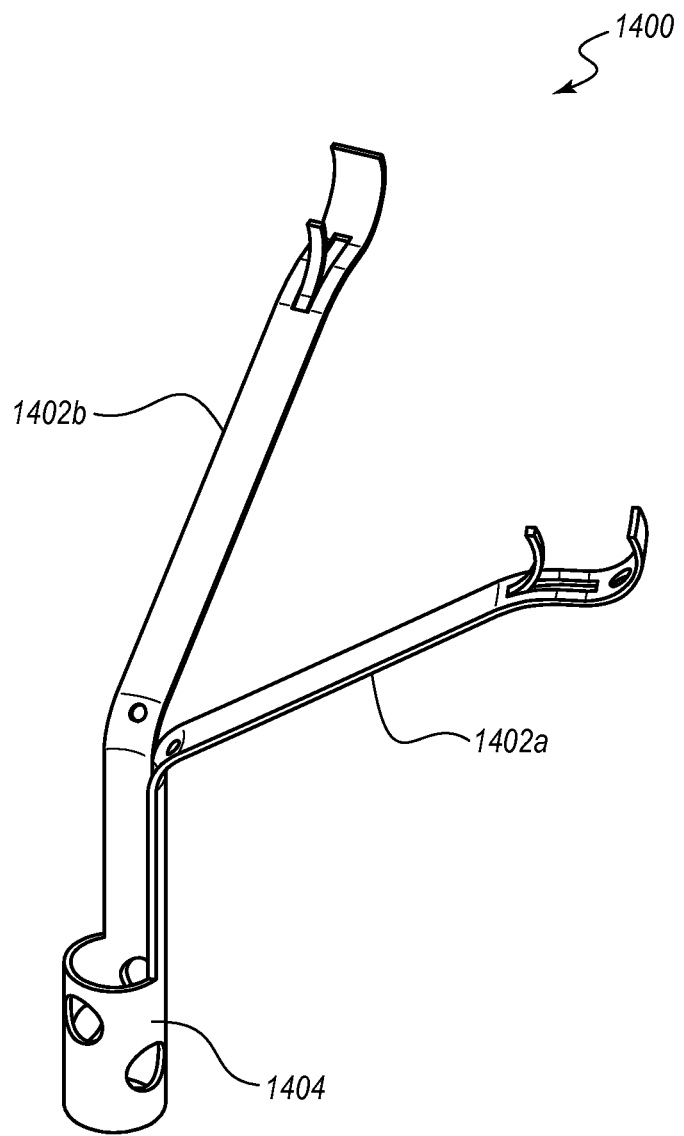
FIGS. 14A and 14B are perspective views of an intimate contact tool of a percutaneous annuloplasty system according to one embodiment.
Figure 14B:
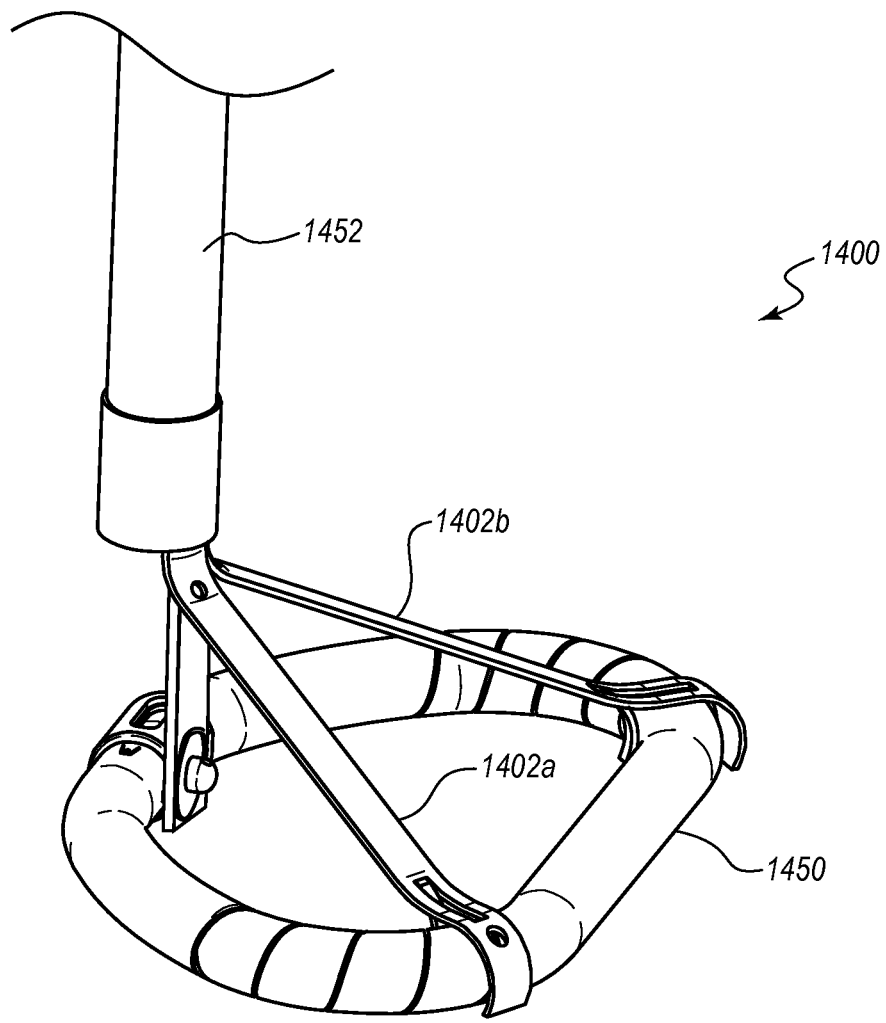

FIGS. 14A and 14B are schematic diagrams illustrating perspective views of an expansion tool 1400 of a percutaneous annuloplasty system according to another embodiment. The intimate contact tool 1400 may be configured to push or press an annuloplasty ring 1450 (from above) into intimate contact with, or abutment against, an annulus of a target heart valve. The illustrated intimate contact tool 1400 includes two arms 1402a, 1402b (collectively 1402) or prongs. FIG. 14A depicts a perspective view of the intimate contact tool 1400 separated from other components of the percutaneous annuloplasty system. FIG. 14B depicts the intimate contact tool 1400 disposed through a delivery catheter 1452 and engaging an annuloplasty ring 1450 from above. The intimate contact tool 1400 may be used to position, orient, and otherwise manipulate the annuloplasty ring 1450 to achieve intimate contact with or abutment against tissue of the annulus of a target heart valve.

The arms 1402 of the intimate contact tool 1400 are configured to extend outward at an angle from a central column 1404, thereby forming a rib structure. The rib structure, and specifically the arms 1402 and central column 1404, may be laser cut from a shape memory material, such as Nitinol. The intimate contact tool 1400 may be cut from a hollow tube to give the central column 1404 a hollow cylindrical shape. The arms 1402 may then be heat set to extend at an angle from the central column 1404.

The illustrated intimate contact tool 1400 of FIGS. 14A and 14B includes two arms 1402a, 1402b arranged, for example, in the shape of a bipod. The two arms 1402a, 1402b in cooperation with a ring shuttle 1454 of the percutaneous annuloplasty system form a tripod structure engaging the annuloplasty ring 1450 at three points. The plurality of arms 1402 may be loaded into a delivery catheter 1452 together with the annuloplasty ring 1450 (e.g., configured in the elongate insertion geometry). As the arms 1402 emerge from a distal end of the delivery catheter 1452 they may automatically expand outward and may be configured to align with and engage the annuloplasty ring 1450 as shown in FIG. 14B. When aligned and engaged with the annuloplasty ring 1450, the intimate contact tool 1400 can be used to push/pull the annuloplasty ring 1450 toward the tissue of an annulus of a heart valve.

The illustrated intimate contact tool of FIGS. 14A and 14B may be configured to engage a top surface of the annuloplasty ring 1450 from above to push the annuloplasty ring 1450. For example, the plurality of arms 1402 may include a curved, angled, or hooked portion at a distal end to facilitate engagement with the annuloplasty ring 1450. The intimate contact tool 1400 can be used to push the annuloplasty ring 1450 from above downward toward the heart valve to facilitate intimate contact of the annuloplasty ring 1450 with the annulus to enhance an anchor deployment process to fasten the annuloplasty ring 1450 to the annulus.

The intimate contact tool 1400, and specifically the arms 1402, may also be configured to function as an expansion tool to engage the annuloplasty ring 1450 and effectuate and/or facilitate transition of the annuloplasty ring 1450 from a contracted state to an expanded state. For example, a superelastic property and memorized shape of the plurality of arms 1402 may enable the arms 1402 to engage an inner surface of the annuloplasty ring 1450 and exert outward force to expand the annuloplasty ring 1450. The intimate contact tool 1400 may be manipulated to sandwich the annuloplasty ring 1450 between the annulus of the target valve, or otherwise press the annuloplasty ring 1450 against the valve, and thereby effectuate expansion of the annuloplasty ring 1450 to the expanded state. In other embodiments, a suture or other elongate member may enable percutaneous manipulation of one or more of the plurality of arms 1402 to effectuate expansion of the annuloplasty ring 1450.

Example Ring Closure Lock Components

FIG. 15A is a schematic diagram illustrating a perspective view of an angled snap 1502 of a ring closure lock (see, e.g., the ring closure lock 106 of FIGS. 1A and 1B) according to one embodiment. FIG. 15B is a schematic diagram illustrating a top view of the angled snap 1502 of FIG. 15A. The ring closure lock may include both the angled snap 1502 having a male configuration and a receiving component (not shown, but see FIGS. 16A and 16B) having a female configuration that is configured to receive the male components 1506, 1508 of the angled snap 1502. The angled snap 1502 may include a first male component 1506 and a second male component 1508 protruding from a base 1504.

Figure 15C:
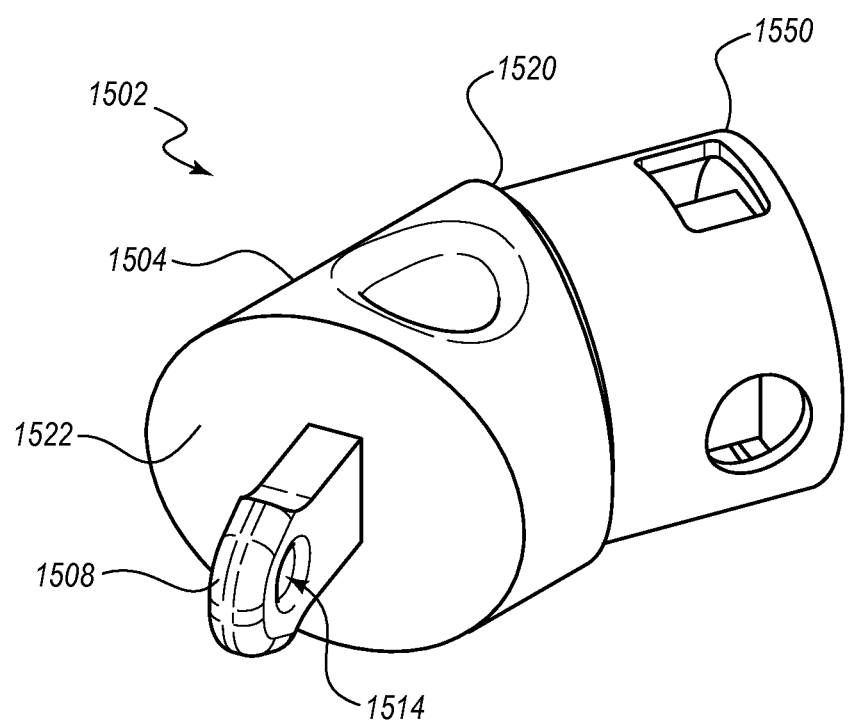
FIG. 15C is a perspective view of the angled snap of the ring closure lock of FIG. 15A.

The first male component 1506 may be configured to securely couple the angled snap 1502 to, for example, a distal end of an annuloplasty ring 1550, as shown in FIG. 15C. The angled snap 1502 may be coupled to the annuloplasty ring 1550 by a pin (not shown) disposed transversely through a distal end of the annuloplasty ring 1550 and a hole 1512 through the first male component 1506.

The second male component 1508 may comprise a bendable tab to enable coupling to a proximal end (see, e.g., FIGS. 16A and 16B) of the annuloplasty ring 1550 from a variety of angles. The second male component 1508 may have a first dimension that is relatively thin to allow the second male component 1508 to be bent in a direction of that first dimension and may have a second dimension that is relatively thick to make the second male component 1508 rigid in a direction of the second dimension. A hole 1514 through the second male component 1508 may receive a snapping suture (see, e.g., suture 919 of FIGS. 9A-9C) configured to be pulled or otherwise percutaneously manipulated to draw and/or snap together the ends of the annuloplasty ring 1550 to transition the annuloplasty ring 1550 from the elongate insertion geometry to the annular operable geometry. The second male component 1508 may couple to the proximal end of the annuloplasty ring 1550 by being received into a receiving component of the ring closure lock, such as the receiving component shown in FIGS. 16A and 16B and described below with reference to the same.

The first male component 1506 and second male component 1508 may be angled relative to each other to facilitate coupling the ends of the annuloplasty ring 1550 at an apex of a curved posterior side of the annuloplasty ring 1550. The annular operable geometry of the annuloplasty ring 1550 may be a D-shape, and a relative angle θ of the first male component 1506 and second male component 1508 may facilitate coupling the ends of the annuloplasty ring 1550 at the apex of the D-shape, such as in the example embodiment of FIGS. 1A and 1B. Described differently, the base 1504 may define a longitudinal axis L and one or both of the first male component 1506 and second male component 1508 may be disposed at angles $\alpha_1$, $\alpha_2$, respectively, to the longitudinal axis L, as shown in FIG. 15B. The first male component 1506 and second male component 1508, because they are disposed at an angle (angles $\alpha_1$, $\alpha_2$, respectively), may aid in coupling a proximal end and a distal end of the annuloplasty ring 1550 to transition the annuloplasty ring 1550 from the elongate insertion geometry to the annular operable geometry and may further aid in defining a D-shape annular operable geometry of the annuloplasty ring 1550. In the illustrated embodiment, the angle $\alpha_1$ and the angle $\alpha_2$ may be the same, or approximately the same. In other embodiments, the angles $\alpha_1$, $\alpha_2$ may be different.

The base 1504 may include a distal ring interface surface 1520 and a proximal ring interface surface 1522 to abut or otherwise interface with the distal end of the annuloplasty ring 1550 and the proximal end of the annuloplasty ring 1550, respectively. The first male component 1506 may extend from the distal ring interface surface 1520, and the second male component 1508 may extend from the proximal ring interface surface 1522. The distal ring interface surface 1520 and the proximal ring interface surface 1522 may be angled relative to each other to aid in defining a D-shape annular operable geometry of the annuloplasty ring 1550.

Although the illustrated embodiment of the angled snap 1502 may be described herein with the first male component 1506 being configured to extend from the distal ring interface surface 1520 to securely couple to the distal end of the annuloplasty ring 1550, skilled artisans appreciate that a mirror configuration is possible wherein the first male component 1506 extends from the proximal ring interface surface 1522 to securely engage the proximal end of the annuloplasty ring 1550 and correspondingly the second male component 1508 extends from the distal ring interface surface 1520 to enable coupling to the distal end of the annuloplasty ring 1550. As noted above, the second male component 1508 may comprise a bendable tab configured to be inserted into a receiving component of a ring closure lock.

Figure 16A:
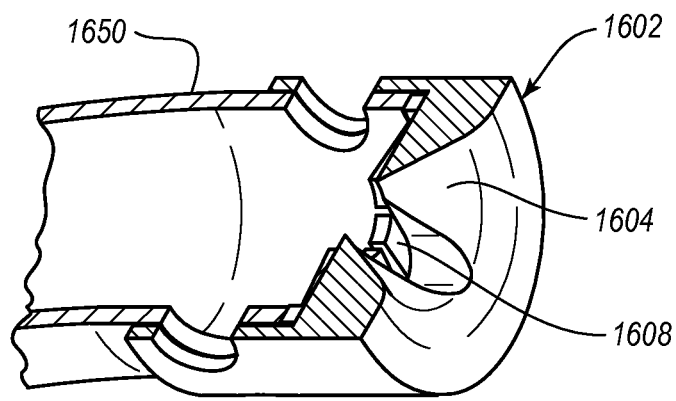
FIGS. 16A and 16B are cross-section views of a receiving component of a ring closure lock according to one embodiment.
Figure 16B:
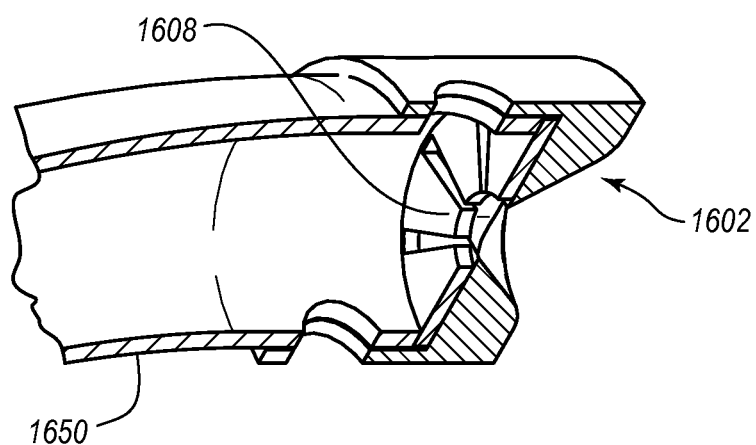
Figure 16C:
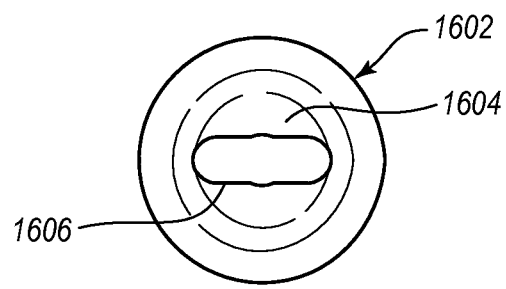
FIG. 16C is an end view of the receiving component of the ring closure lock of FIGS. 16A and 16B according to one embodiment.

FIGS. 16A and 16B are schematic diagrams illustrating perspective cross-section views of a receiving component 1602 of a ring closure lock (see, e.g., ring closure lock 106 of FIGS. 1A and 1B) according to one embodiment. FIG. 16C is a schematic diagram illustrating an end view of the receiving component 1602 of FIGS. 16A and 16B. Referring generally and collectively to FIGS. 16A-16C, the illustrated receiving component 1602 is coupled to a proximal end of an annuloplasty ring 1650. Skilled artisans appreciate that, in other embodiments, the receiving component 1602 may be coupled to a distal end of the annuloplasty ring 1650. The receiving component 1602 may be configured to receive a male component of a snap component of the ring closure lock. For example, the receiving component 1602 may be configured to receive the second male component 1508 of the angled snap 1502 of FIGS. 15A-15C.

The illustrated receiving component 1602 of FIGS. 16A-16C may include a conical cavity 1604 tapering to a slot 1606 sized and shaped to receive the male component. The conical cavity 1604 allows a leading portion of the male component to smoothly enter the slot 1606 in the receiving component 1602 even if the male component and the slot 1606 are not perfectly aligned when they meet. The slot 1606 may have appropriate dimensions to allow the male component, with a suture placed through it, to pass through without any interference. The suture can be used to percutaneously pull the male component through the slot 1606.

The receiving component 1602 may further include a snapping disk 1608 that may be disposed at the slot 1606 at a side opposite or behind the conical cavity 1604, in abutment with or otherwise adjacent to the annuloplasty ring 1650. The snapping disk 1608 may allow a male component to enter the slot 1606 from the conical cavity 1604, but may restrict or prevent the male component from exiting or being retracted back through the slot 1606. As illustrated, the snapping disk 1608 may comprise a plurality of tabs configured to engage a male component. In other embodiments, the receiving component may not include a snapping disk 1608, but rather the tabs can be laser cut when the body member of the annuloplasty ring 1650 is cut and the tabs can be bent inside to perform a similar function as the snapping disk 1608.

Example Proximal End Handle

Figure 17A:
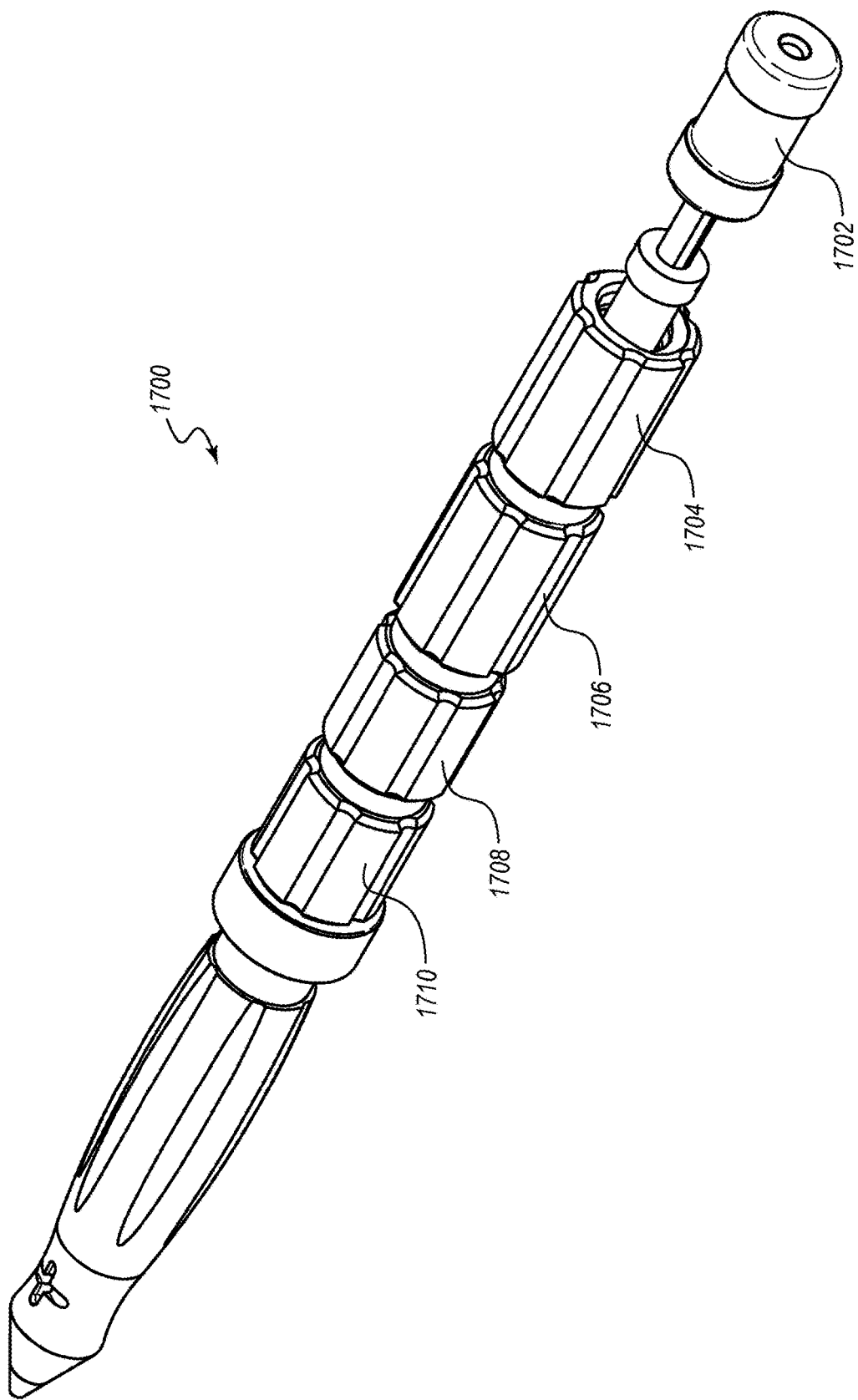
FIG. 17A is a perspective view of a proximal end handle of a percutaneous annuloplasty system according to one embodiment.
Figure 17B:
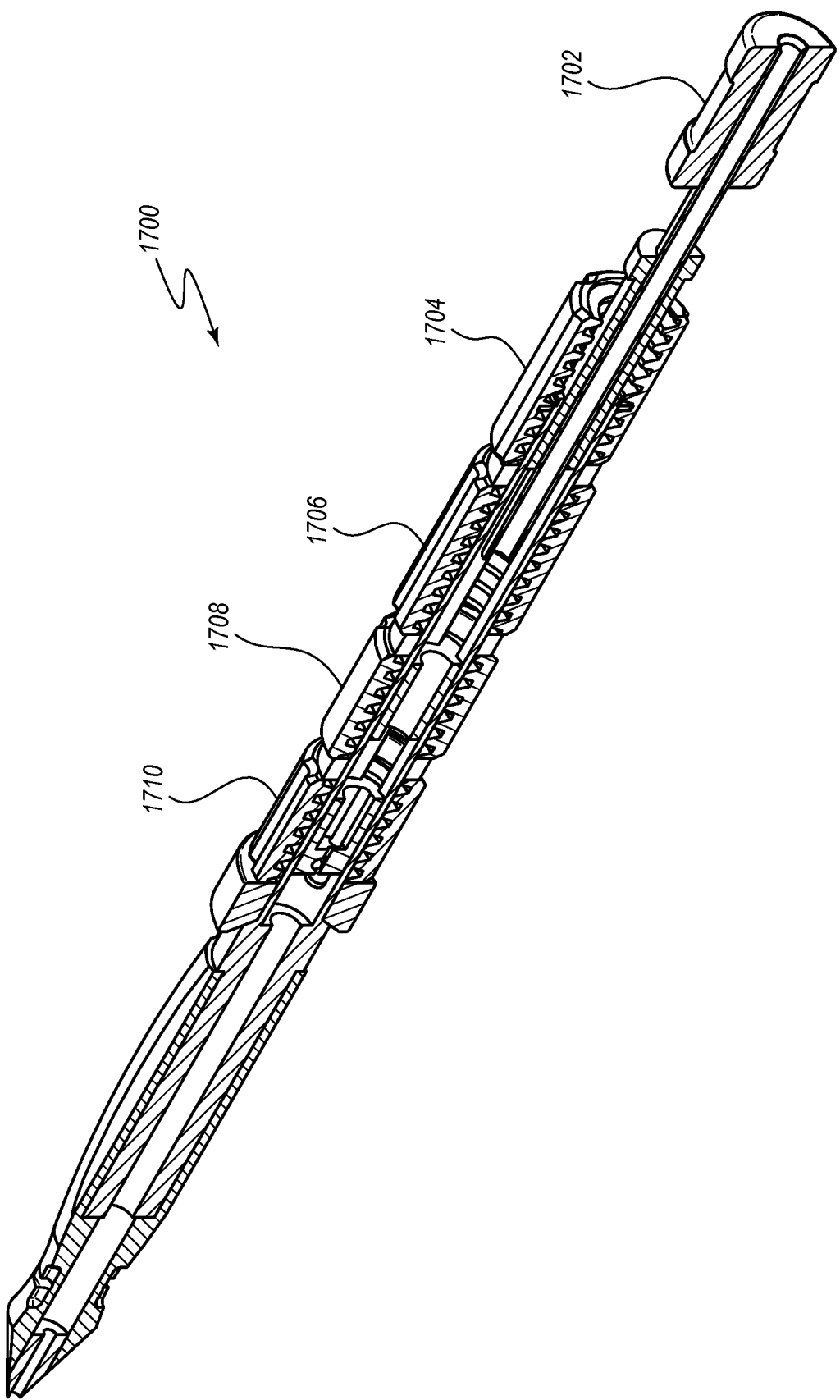
FIG. 17B is cross-section view of the proximal end handle of FIG. 17A.

FIG. 17A is a schematic diagram illustrating a perspective view of a proximal end handle 1700 of a percutaneous annuloplasty system according to one embodiment. FIG. 17B is a schematic diagram illustrating a perspective cross-section view of the proximal end handle 1700 of FIG. 17A. The proximal end handle 1700 may enable percutaneous transcatheter deployment of an annuloplasty ring. More particularly, the proximal end handle 1700 may enable percutaneous manipulation of an annuloplasty system configured to deliver, configure, and orient an annuloplasty ring and to fasten the annuloplasty ring to the annulus of a target heart valve.

The illustrated embodiment of a proximal end handle may comprise various rotating knobs that perform or enable various functions. There may be a rotatable knob for each function to be performed. A ring closure knob 1702 may enable closure of the annuloplasty ring to transition from an elongate insertion geometry to an annular operable geometry. A ring snap knob 1704 may enable snapping together of first and second ends (e.g., distal and proximal ends) of the annuloplasty ring or other manipulation of a ring closure lock. An anchor deployment knob 1706 may enable deployment of anchors of an annuloplasty ring to fasten the annuloplasty ring to the annulus of the target heart valve. An A-P adjustment knob 1708 may enable contraction of the annuloplasty ring from an expanded state to a contracted state. In other embodiments, the A-P adjustment knob 1708 may also enable manipulation of an expansion tool to facilitate expansion of the annuloplasty ring to an expanded state (e.g., prior to deployment of the anchors). A ring release knob 1710 may enable release of the annuloplasty ring from a delivery system and/or delivery shuttle of a percutaneous annuloplasty system. Additional or fewer knobs may be possible, as dependent on functions to be performed.

Each of the knobs 1702, 1704, 1706, 1708, 1710 may be coupled to and manipulate an independent system of cables or sutures by rotating the respective knob 1702, 1704, 1706, 1708, 1710. As shown in FIG. 17B, each of the knobs 1702, 1704, 1706, 1708, 1710 may be mechanically coupled to a translation gear mechanism. The gear mechanism may be connected to a pulling cable or suture that is configured to perform a given function.

Example Methods for Percutaneous Annuloplasty

Figure 18:
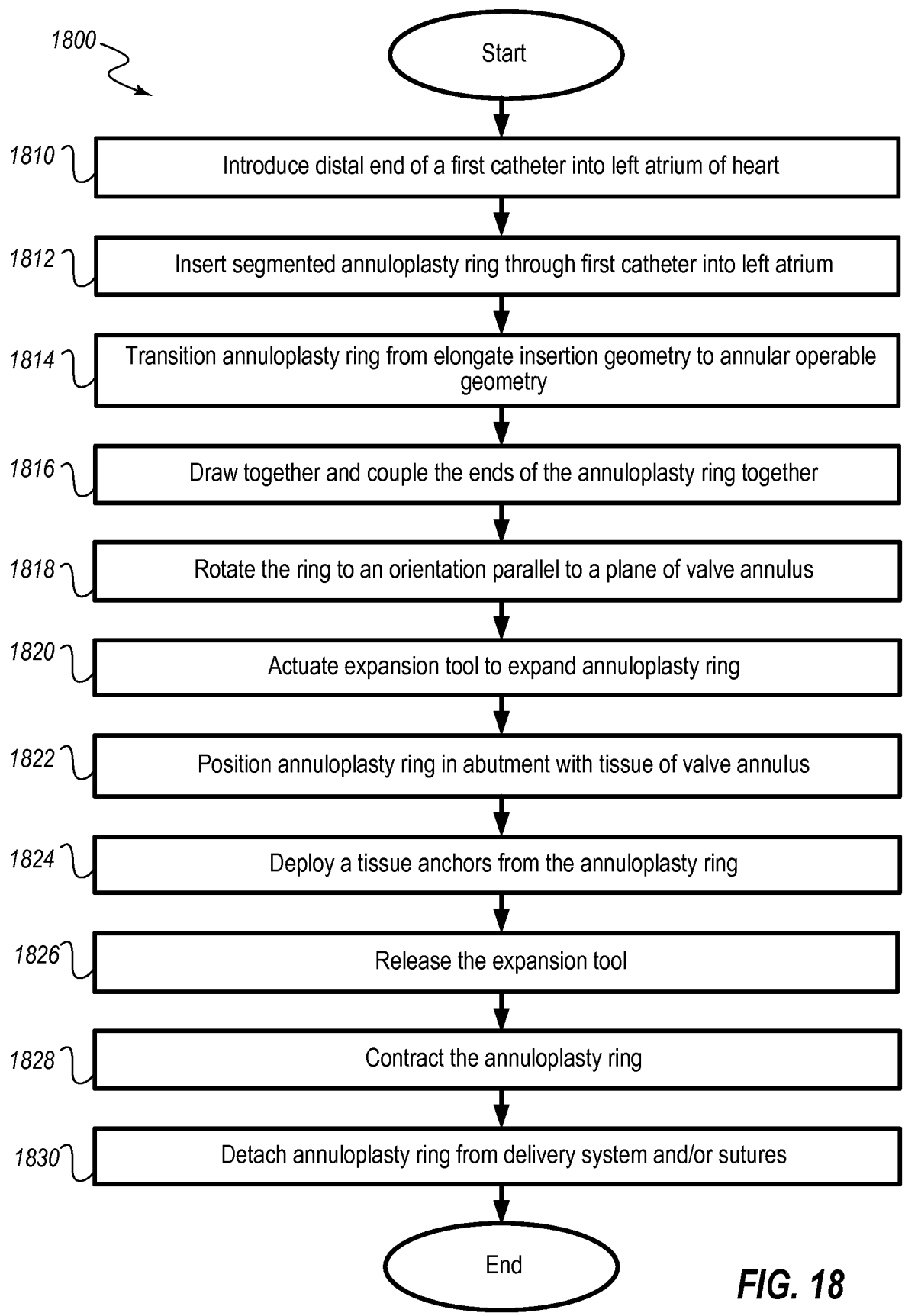
FIG. 18 is a flowchart of a method for repairing a defective heart valve according to one embodiment.

FIG. 18 is a flowchart of a method 1800 for repairing a defective heart valve according to one embodiment. The method 1800 includes percutaneously introducing 1810 a distal end of a first catheter into a left atrium of a heart and inserting 1812 a annuloplasty ring, attached to a second catheter, through the first catheter into the left atrium. The annuloplasty ring may include a superelastic shape memory material that may aid to transition 1814 the annuloplasty ring from an elongate insertion geometry to an annular operable geometry as the annuloplasty ring exits the distal end of the first catheter. The method 1800 may include pulling 1816 a first suture, connected to the annuloplasty ring through the second catheter, to draw together and couple the ends of the annuloplasty ring together, for example at a ring closure lock.

The method 1800 may further include automatically rotating 1818 the annuloplasty ring to change a plane of the annuloplasty ring from a first orientation that is parallel to the second catheter to a second orientation that is parallel to a plane of the mitral valve annulus. A percutaneously, transcatheter-operated expansion tool may be actuated 1820 to expand the annuloplasty ring in the annular operable geometry to an expanded state to thereby increase an A-P distance of the annuloplasty ring. Expansion of the annuloplasty ring may include expanding a biasing element of the annuloplasty ring.

The method 1800 may include positioning 1822 the annuloplasty ring in abutment or similar relatively intimate contact with an annulus of a target valve of the heart to enhance a process of fastening the annuloplasty ring to the annulus of the target heart valve. The method 1800 may include pulling a second suture, connected to the annuloplasty ring through the second catheter, to deploy 1824 a plurality of tissue anchors from the annuloplasty ring. With the anchors deployed and the annuloplasty ring fastened to the tissue of the target heart valve, the expansion tool may be released 1826. The annuloplasty ring may be contracted 1828 to transition the annuloplasty ring in the operable geometry to a contracted state to decrease the A-P distance and thereby decrease the A-P distance of the target heart valve to improve coaptation and reduce regurgitation through the target heart valve. In certain embodiments, contraction 1828 of the annuloplasty ring may be accomplished by biasing elements that have stored potential energy during expansion of the annuloplasty ring.

The method 1800 may further include detaching 1830 the annuloplasty ring from the second catheter and the first and second sutures, and remove the first and second catheters from the heart.

Those having skill in the art will understand from the disclosure herein that many changes may be made to the details of the above-described embodiments without departing from the underlying principles of the invention. The scope of the present invention should, therefore, be determined only by the following claims.

What is claimed is:

1. An adjustable annuloplasty ring for percutaneous, transcatheter heart valve repair, the annuloplasty ring comprising:
   a body member comprising at least three sections, wherein the body member is transitionable from an elongate insertion geometry to an annular operable geometry,
   a plurality of anchors percutaneously deployable from the body member in the annular operable geometry to engage the annulus of a target valve; and
   at least two biasing elements, wherein each biasing element is separated from any other biasing element by at least one of the at least three sections wherein the at least two biasing elements are configured to expand or contract independently of each other, and
   wherein the two or more biasing elements bias the annuloplasty ring in the operable geometry toward a contracted state such that expansion of the annuloplasty ring to an expanded state stores a potential energy in the two or more biasing elements,
   wherein the at least two biasing elements each comprise an integral biasing portion of the body member,
   wherein the integral biasing portion of the body member comprises a spiral cut in a portion of the body member to form a spiral shape in the body member that is expandable to the expanded state and that is biased toward the contracted state.

2. The adjustable annuloplasty ring of claim 1, wherein the target valve is a mitral valve.

3. The adjustable annuloplasty ring of claim 2, wherein the elongate insertion geometry allows percutaneous passage of the annuloplasty ring, via a catheter, into a heart of a patient comprising an endovascular delivery into the heart of the patient.

4. The adjustable annuloplasty ring of claim 3, wherein the endovascular delivery into the heart comprises a trans-septal approach.

5. The adjustable annuloplasty ring of claim 3, wherein the endovascular delivery into the heart comprises a retrograde approach.

6. The adjustable annuloplasty ring of claim 1, wherein the elongate insertion geometry allows percutaneous passage of the annuloplasty ring, via a catheter, into the heart of the patient comprising a trans-apical approach.

7. The adjustable annuloplasty ring of claim 1, wherein expansion of the at least two biasing elements decreases the anterior-posterior distance of the annuloplasty ring between 3 mm and 5 mm.

8. The adjustable annuloplasty ring of claim 7, wherein the annular operable geometry forms a D-shaped ring.

9. The adjustable annuloplasty ring of claim 7, wherein the at least two biasing elements are configured to be actuated percutaneously by an elongate mechanical coupling extending from the biasing element, through the catheter, to a position external to a body of the patient.

10. The adjustable annuloplasty ring of claim 9, wherein the elongate mechanical coupling comprises a suture.

11. The adjustable annuloplasty ring of claim 9, wherein the mechanical coupling comprises a cable.

12. The adjustable annuloplasty ring of claim 7, wherein actuation of the at least two biasing elements comprises releasing the at least two biasing elements.

13. The adjustable annuloplasty ring of claim 7, the body member forming an outer hollow member, wherein adjacent regions of the body member cooperate with one another to change the outer hollow member from the elongate insertion geometry to the annular operable geometry, the adjustable annuloplasty ring further comprising:
an internal anchor member located at least partially within the outer hollow member, the internal anchor member comprising the plurality of anchors, and the internal anchor member configured to move the plurality of anchors with respect to a plurality of windows in the outer hollow member to selectively deploy the plurality of anchors through corresponding windows.

14. The adjustable annuloplasty ring of claim 7,
wherein the at least two biasing elements comprise a first biasing element and a second biasing element,
wherein the at least three sections comprise a first posterior region, a second posterior region and an anterior region, and
wherein the first biasing element is disposed between the first posterior region and the anterior region and the second biasing element is disposed between the second posterior region and the anterior region.

15. The adjustable annuloplasty ring of claim 7, wherein the plurality of anchors deploy from the at least three sections of the body member.

16. The adjustable annuloplasty ring of claim 7, wherein the at least two biasing elements are configured to lengthen or shorten an overall circumference of the adjustable annuloplasty ring.

* * * * *